(12) United States Patent
Takeyama et al.

(10) Patent No.: US 8,252,287 B2
(45) Date of Patent: Aug. 28, 2012

(54) BLOOD COAGULATION FACTOR VIII ACTIVATION-ENHANCING ANTIBODIES

(75) Inventors: Masahiro Takeyama, Nara (JP); Keiji Nogami, Nara (JP); Midori Shima, Nara (JP); Tsukasa Suzuki, Shizuoka (JP)

(73) Assignees: Chugai Seiyaku Kabushiki Kaisha, Tokyo (JP); Nara Medical University, Nara (JP)

( * ) Notice: Subject to any disclaimer, the term of this patent is extended or adjusted under 35 U.S.C. 154(b) by 371 days.

(21) Appl. No.: 12/395,909

(22) Filed: Mar. 2, 2009

(65) Prior Publication Data

US 2009/0297503 A1 Dec. 3, 2009

Related U.S. Application Data

(63) Continuation-in-part of application No. PCT/JP2007/066982, filed on Aug. 31, 2007.

(30) Foreign Application Priority Data

Aug. 31, 2006 (JP) ................................ 2006-235776

(51) Int. Cl.
*A61K 39/395* (2006.01)
(52) U.S. Cl. ............... 424/145.1; 424/133.1; 424/141.1; 514/14.1; 530/387.3; 530/388.1; 530/388.25
(58) Field of Classification Search ........................ None
See application file for complete search history.

(56) References Cited

U.S. PATENT DOCUMENTS 7,858,089 B2 * 12/2010 Jacquemin et al. ........ 424/133.1
2007/0041978 A1 * 2/2007 Hattori et al. ............. 424/146.1

FOREIGN PATENT DOCUMENTS

WO WO 03/093313 A2 11/2003
WO WO 2005035756 A1 * 4/2005

OTHER PUBLICATIONS

Scandella et al., Blood. Sep. 15, 1993;82(6):1767-75.*
Janeway et al., Immunobiology, 3rd edition, 1997, Garland Publications, pp. 3:1-3:11.*
Rudikoff et al. Proc Natl Acad Sci U S A. Mar. 1982;79(6):1979-83.*
Portolano et al., J Immunol. Feb. 1, 1993;150(3):880-7.*
Fundamental Immunology, William E. Paul, M.D. ed., 3d ed. 1993, p. 242.*
Arai, M., "Analysis of the Activation Mechanism of F.VIII/vWF Complex by Anti-human VIII: Ag Monoclonal Antibodies," *Journal of Tokyo Medical College* 45:384-394, Tokyo Medical College (1986).
Batlle, J., et al., "Antibodies to factor VIII in plasma of patients with hemophilia A and normal subjects," *Ann Hematol* 72:321-326, Springer-Verlag (1996).
Blanco, A.N., et al., "An ELISA system to detect anti-factor VIII antibodies without interference by lupus anticoagulants. Preliminary data in hemophilia A patients," *Haematologica* 85:1045-1050, Ferrata Storti Foundation (2000).

Eaton, D., et al., "Proteolytic Processing of Human Factor VIII. Correlation of Specific Cleavages by Thrombin, Factor Xa, and Activated Protein C with Activation and Inactivation of Factor VIII Coagulant Activity," *Biochemistry* 25:505-512, American Chemical Society (1986).
Fay, P.J., "Activation of factor VIII and mechanisms of cofactor action," *Blood Reviews* 18:1-15, Elsevier Ltd. (2004).
Fay, P.J., et al., "The size of human factor VIII heterodimers and the effects produced by thrombin," *Biochimica et Biophysica Acta* 871:268-278, Elsevier Science Publishers B.V. (1986).
Fay, P.J. and Scandella, D., "Human Inhibitor Antibodies Specific for the Factor VIII A2 Domain Disrupt the Interaction between the Subunit and Factor IXa," *The Journal of Biological Chemistry* 274:29826-29830, The American Society for Biochemistry and Molecular Biology, Inc. (1999).
Fay, P.J., et al., "Cleavage of Factor VIII Heavy Chain Is Required for the Functional Interaction of A2 Subunit with Factor IXa," *The Journal of Biological Chemistry* 276:12434-12439, The American Society for Biochemistry and Molecular Biology, Inc. (2001).
Hayashi, A., et al., "Ketsuyubyo ni Hassei shita Dai VIII Inshi Sogai Kotai no Ninshiki suru Dai VIII Inshi epitope," *The Japanese Journal of Clinical Hematology* 32:945-950, Japan Society of Clinical Hematology (1991).
Hoyer, L.W., "The Factor VIII Complex: Structure and Function," *Blood* 58:1-13, The American Society of Hematology (1981).
Leyte, A., et al., "Inhibition of human coagulation Factor VIII by monoclonal antibodies," *Biochem. J.* 263:187-194, Portland Press Ltd. (1989).
Lollar, P., et al., "Association of the Factor VIII Light Chain with von Willebrand Factor," *The Journal of Biological Chemistry* 263:10451-10455, The American Society for Biochemistry and Molecular Biology, Inc. (1988).
Mann, K.G., et al., "Surface-Dependent Reactions of the Vitamin K-Dependent Enzyme Complexes," *Blood* 76:1-16, The American Society of Hematology (1990).
Nogami, K., "Dai VIII Inshi Bunshi to Kasseika Dai X Inshi tono Ketsugo ni Okeru Dai VIII Inshi C2 Domain no Yakuwari," *Japanese Journal of Thrombosis and Hemostasis* 11:436, The Japanese Society on Thrombosis and Hemostasis (2000).
Nogami, K., et al., "Circulating factor VIII immune complexes in patients with type 2 acquired hemophilia A and protection from activated protein C-mediated proteolysis," *Blood* 97:669-677, The American Society of Hematology (2001).
Nogami, K., et al., "Plasmin ni yoru Dai VIII Inshi Fukatsuka Kiko," *Japanese Journal of Thrombosis and Hemostasis* 16:515, The Japanese Society on Thrombosis and Hemostasis (2005).

(Continued)

*Primary Examiner* — Michael Szperka
(74) *Attorney, Agent, or Firm* — Sterne, Kessler, Goldstein & Fox P.L.L.C.

(57) ABSTRACT

For the first time, the present invention provides antibodies that enhance the generation of activated blood coagulation factor VIII. The antibodies enhance the cleavage of blood coagulation factor VIII at the Arg of position 372 and suppress the cleavage at the Arg of position 336 by recognizing and binding to the A2 domain of blood coagulation Factor VIII. Such antibodies are expected to be useful in preventing or treating diseases that develop or progress due to decrease or loss of the blood coagulation factor VIII activity, for example, hemophilia A, acquired hemophilia, and von Willebrand's disease.

11 Claims, 11 Drawing Sheets

OTHER PUBLICATIONS

Nogami, K., et al., "Role of Factor VIII C2 Domain in Factor VIII Binding to Factor Xa," *The Journal of Biological Chemistry* 274:31000-31007, The American Society for Biochemistry and Molecular Biology, Inc. (1999).

Nogami, K., et al., "Factor VIII C2 Domain Contains the Thrombin-binding Site Responsible for Thrombin-catalyzed Cleavage at Arg[1689]," *The Journal of Biological Chemistry* 275:25774-25780, The American Society for Biochemistry and Molecular Biology, Inc. (2000).

Nogami, K., et al., "Identification of a Factor Xa-interactive Site within Residues 337-372 of the Factor VIII Heavy Chain," *The Journal of Biological Chemistry* 279:15763-15771, The American Society for Biochemistry and Molecular Biology, Inc. (2004).

Nogami, K., et al., "Mechanisms of Interactions of Factor X and Factor Xa with the Acidic Region in the Factor VIII A1 Domain," *The Journal of Biological Chemistry* 279:33104-33113, The American Society for Biochemistry and Molecular Biology, Inc. (2004).

Nogami, K., et al., "Dai VIII Inshi A1 Domain Lys36 Oyobi Arg336 Kairetsu ni Motozuku Kasseigata Dai X Inshi ni yoru Kasseigata Dai VIII Inshi Fukatsuka Kiko," *The Japanese Journal of Clinical Hematology* 46:215, Japan Society of Clinical Hematology (2005).

Nogami, K., et al., "Human Factor VIII Inhibitor Alloantibodies with a C2 Epitope Inhibit Factor Xa-catalyzed Factor VIII Activation: A new Anti-factor VIII Inhibitory Mechanism," *Thromb Haemost* 87:459-465, Schattauer GmbH, Stuttgart (2002).

Regan, L.M. and Fay, P.J., "Cleavage of Factor VIII Light Chain Is Required for Maximal Generation of Factor VIIIa Activity," *Journal of Biological Chemistry* 270:8546-8552, The American Society for Biochemistry and Molecular Biology, Inc. (1995).

Scandella, D., et al., "Some Factor VIII Inhibitor Antibodies Recognize a Common Epitope Corresponding to C2 Domain Amino Acids 2248 Through 2312, Which Overlap a Phospholipid-Binding Site," *Blood* 86:1811-1819, The American Society of Hematology (1995).

Shima, M., "Characterization of Factor VIII Inhibitors," *International Journal of Hematology* 83:109-118, The Japanese Society of Hematology (2006).

Shima, M., et al., "Common inhibitory effects of human anti-C2 domain inhibitor alloantibodies on factor VIII binding to von Willebrand factor," *British Journal of Haematology* 91:714-721, Blackwell Science Ltd. (1995).

Shima, M., et al., "A Factor VIII Neutralizing Monoclonal Antibody and a Human Inhibitor Alloantibody Recognizing Epitopes in the C2 Domain Inhibit Factor VIII Binding to von Willebrand Factor and to Phosphatidylserine," *Thrombosis and Haemostasis* 69:240-246, F.K. Schattauer Verlagsgesellschaft mbH, Stuttgart (1993).

Takeyama, M., et al., "Dai VIII Inshi Kassei Zokyo Sayo o Yusuru Dai VIII Inshi (FVIII) A1/A3 Domain Ninshiki Kotai," *The Japanese Journal of Clinical Hematology* 47:269, Japan Society of Clinical Hematology (2006).

Vehar, G.A., et al., "Structure of human factor VIII," *Nature* 312:337-342, The Nature Publishing Company (1984).

Wood, W.I., et al., "Expression of active human factor VIII from recombinant DNA clones," *Nature* 312:330-337, The Nature Publishing Company (1984).

Zhong, D., et al., "Some Human Inhibitor Antibodies Interfere With Factor VIII Binding to Factor IX," *Blood* 92:136-142, The American Society of Hematology (1998).

International Search Report for International Application No. PCT/JP2007/066982, mailed Nov. 13, 2007, Japanese Patent Office, Tokyo, Japan.

* cited by examiner

SEQUENCE LISTING

<160> NUMBER OF SEQ ID NOS: 13

<210> SEQ ID NO 1
<211> LENGTH: 121
<212> TYPE: PRT
<213> ORGANISM: Mus musculus

<400> SEQUENCE: 1

```
Glu Val Arg Leu Val Glu Ser Gly Gly Gly Leu Val Lys Pro Gly Gly
1               5                   10                  15

Ser Leu Lys Leu Ser Cys Ala Ala Ser Glu Phe Thr Phe Ser Ser Tyr
            20                  25                  30

Ser Met Ser Trp Val Arg Gln Thr Pro Glu Lys Arg Leu Glu Trp Val
        35                  40                  45

Ala Ser Ile Asn Ser Gly Gly Arg Thr Phe Tyr Pro Asp Ser Val Lys
    50                  55                  60

Gly Arg Phe Thr Ile Ser Arg Asp Asn Ala Arg Asn Ile Leu Val Leu
65                  70                  75                  80

Gln Met Ser Ser Leu Arg Ser Glu Asp Thr Ala Met Tyr Tyr Cys Ala
                85                  90                  95

Arg Val Ile Tyr Tyr Asp Tyr Gly Ala Tyr Ala Leu Asp Tyr Trp Gly
            100                 105                 110

Gln Gly Thr Ser Leu Thr Val Ser Ser
        115                 120
```

<210> SEQ ID NO 2
<211> LENGTH: 5
<212> TYPE: PRT
<213> ORGANISM: Mus musculus

<400> SEQUENCE: 2

```
Ser Tyr Ser Met Ser
1               5

<210> SEQ ID NO 3
<211> LENGTH: 16
<212> TYPE: PRT
<213> ORGANISM: Mus musculus

<400> SEQUENCE: 3

Ser Ile Asn Ser Gly Gly Arg Thr Phe Tyr Pro Asp Ser Val Lys Gly
1               5                   10                  15

<210> SEQ ID NO 4
<211> LENGTH: 13
<212> TYPE: PRT
<213> ORGANISM: Mus musculus

<400> SEQUENCE: 4

Val Ile Tyr Tyr Asp Tyr Gly Ala Tyr Ala Leu Asp Tyr
1               5                   10

<210> SEQ ID NO 5
<211> LENGTH: 140
<212> TYPE: PRT
<213> ORGANISM: Mus musculus
<220> FEATURE:
<221> NAME/KEY: SIGNAL
<222> LOCATION: (1)..(19)
<220> FEATURE:
<221> NAME/KEY: MISC_FEATURE
<222> LOCATION: (50)..(54)
<223> OTHER INFORMATION: Complementarity Determinig Region
<220> FEATURE:
<221> NAME/KEY: MISC_FEATURE
<222> LOCATION: (69)..(84)
<223> OTHER INFORMATION: Complementarity Determinig Region
<220> FEATURE:
<221> NAME/KEY: MISC_FEATURE
<222> LOCATION: (117)..(129)
<223> OTHER INFORMATION: Complementarity Determinig Region

<400> SEQUENCE: 5

Met Asn Phe Gly Phe Ser Leu Ile Phe Leu Val Leu Val Leu Lys Gly
1               5                   10                  15

Val Gln Cys Glu Val Arg Leu Val Glu Ser Gly Gly Gly Leu Val Lys
            20                  25                  30

Pro Gly Gly Ser Leu Lys Leu Ser Cys Ala Ala Ser Glu Phe Thr Phe
        35                  40                  45

Ser Ser Tyr Ser Met Ser Trp Val Arg Gln Thr Pro Glu Lys Arg Leu
    50                  55                  60

Glu Trp Val Ala Ser Ile Asn Ser Gly Gly Arg Thr Phe Tyr Pro Asp
65                  70                  75                  80

Ser Val Lys Gly Arg Phe Thr Ile Ser Arg Asp Asn Ala Arg Asn Ile
                85                  90                  95

Leu Val Leu Gln Met Ser Ser Leu Arg Ser Glu Asp Thr Ala Met Tyr
            100                 105                 110

Tyr Cys Ala Arg Val Ile Tyr Tyr Asp Tyr Gly Ala Tyr Ala Leu Asp
        115                 120                 125

Tyr Trp Gly Gln Gly Thr Ser Leu Thr Val Ser Ser
    130                 135                 140

<210> SEQ ID NO 6
<211> LENGTH: 108
<212> TYPE: PRT
<213> ORGANISM: Mus musculus
```

<400> SEQUENCE: 6

Glu Ile Val Leu Thr Gln Ser Pro Ala Leu Met Ala Tyr Pro Gly
1               5                   10                  15

Glu Lys Val Thr Ile Thr Cys Ser Val Ser Ser Ser Ile Ser Ser
            20                  25                  30

Asn Leu His Trp Tyr Gln Gln Lys Ser Glu Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Asn Ile Tyr Pro
                85                  90                  95

Leu Thr Phe Gly Ala Gly Thr Lys Leu Glu Leu Lys
            100                 105

<210> SEQ ID NO 7
<211> LENGTH: 12
<212> TYPE: PRT
<213> ORGANISM: Mus musculus

<400> SEQUENCE: 7

Ser Val Ser Ser Ser Ile Ser Ser Ser Asn Leu His
1               5                   10

<210> SEQ ID NO 8
<211> LENGTH: 7
<212> TYPE: PRT
<213> ORGANISM: Mus musculus

<400> SEQUENCE: 8

Gly Thr Ser Asn Leu Ala Ser
1               5

<210> SEQ ID NO 9
<211> LENGTH: 9
<212> TYPE: PRT
<213> ORGANISM: Mus musculus

<400> SEQUENCE: 9

Gln Gln Trp Asn Ile Tyr Pro Leu Thr
1               5

<210> SEQ ID NO 10
<211> LENGTH: 130
<212> TYPE: PRT
<213> ORGANISM: Mus musculus
<220> FEATURE:
<221> NAME/KEY: SIGNAL
<222> LOCATION: (1)..(22)
<220> FEATURE:
<221> NAME/KEY: MISC_FEATURE
<222> LOCATION: (46)..(57)
<223> OTHER INFORMATION: Complementarity Determinig Region
<220> FEATURE:
<221> NAME/KEY: MISC_FEATURE
<222> LOCATION: (73)..(79)
<223> OTHER INFORMATION: Complementarity Determinig Region
<220> FEATURE:
<221> NAME/KEY: MISC_FEATURE
<222> LOCATION: (112)..(120)
<223> OTHER INFORMATION: Complementarity Determinig Region

<400> SEQUENCE: 10

```
Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Tyr Pro Gly Glu Lys Val Thr Ile Thr Cys Ser Val Ser
            35                  40                  45

Ser Ser Ile Ser Ser Ser Asn Leu His Trp Tyr Gln Gln Lys Ser Glu
        50                  55                  60

Thr Ser Pro Lys Leu Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
                100                 105                 110

Gln Trp Asn Ile Tyr Pro Leu Thr Phe Gly Ala Gly Thr Lys Leu Glu
            115                 120                 125

Leu Lys
    130

<210> SEQ ID NO 11
<211> LENGTH: 2351
<212> TYPE: PRT
<213> ORGANISM: Homo sapiens
<300> PUBLICATION INFORMATION:
<308> DATABASE ACCESSION NUMBER: GENBANK/NP_000123
<309> DATABASE ENTRY DATE: 2006-08-20
<313> RELEVANT RESIDUES IN SEQ ID NO: (1)..(2351)

<400> SEQUENCE: 11

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220
```

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
            245                 250                 255

Val Asn Arg Ser Leu Pro Gly Leu Ile Gly Cys His Arg Lys Ser Val
        260                 265                 270

Tyr Trp His Val Ile Gly Met Gly Thr Thr Pro Glu Val His Ser Ile
    275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
```

```
                    645                 650                 655
Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
                980                 985                 990

Lys Gly Lys Arg Ala His Gly Pro Ala Leu Leu Thr Lys Asp Asn Ala
                995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065
```

-continued

| | | | | | | | | | | | |
|---|---|---|---|---|---|---|---|---|---|---|---|
| Met | Leu | Met | Asp | Lys | Asn | Ala | Thr | Ala | Leu | Arg | Leu | Asn | His | Met |
| | 1070 | | | | 1075 | | | | 1080 | | |

Met Leu Met Asp Lys Asn Ala Thr Ala Leu Arg Leu Asn His Met
1070            1075                1080

Ser Asn Lys Thr Thr Ser Ser Lys Asn Met Glu Met Val Gln Gln
1085            1090                1095

Lys Lys Glu Gly Pro Ile Pro Pro Asp Ala Gln Asn Pro Asp Met
1100            1105                1110

Ser Phe Phe Lys Met Leu Phe Leu Pro Glu Ser Ala Arg Trp Ile
1115            1120                1125

Gln Arg Thr His Gly Lys Asn Ser Leu Asn Ser Gly Gln Gly Pro
1130            1135                1140

Ser Pro Lys Gln Leu Val Ser Leu Gly Pro Glu Lys Ser Val Glu
1145            1150                1155

Gly Gln Asn Phe Leu Ser Glu Lys Asn Lys Val Val Val Gly Lys
1160            1165                1170

Gly Glu Phe Thr Lys Asp Val Gly Leu Lys Glu Met Val Phe Pro
1175            1180                1185

Ser Ser Arg Asn Leu Phe Leu Thr Asn Leu Asp Asn Leu His Glu
1190            1195                1200

Asn Asn Thr His Asn Gln Glu Lys Lys Ile Gln Glu Glu Ile Glu
1205            1210                1215

Lys Lys Glu Thr Leu Ile Gln Glu Asn Val Val Leu Pro Gln Ile
1220            1225                1230

His Thr Val Thr Gly Thr Lys Asn Phe Met Lys Asn Leu Phe Leu
1235            1240                1245

Leu Ser Thr Arg Gln Asn Val Glu Gly Ser Tyr Asp Gly Ala Tyr
1250            1255                1260

Ala Pro Val Leu Gln Asp Phe Arg Ser Leu Asn Asp Ser Thr Asn
1265            1270                1275

Arg Thr Lys Lys His Thr Ala His Phe Ser Lys Lys Gly Glu Glu
1280            1285                1290

Glu Asn Leu Glu Gly Leu Gly Asn Gln Thr Lys Gln Ile Val Glu
1295            1300                1305

Lys Tyr Ala Cys Thr Thr Arg Ile Ser Pro Asn Thr Ser Gln Gln
1310            1315                1320

Asn Phe Val Thr Gln Arg Ser Lys Arg Ala Leu Lys Gln Phe Arg
1325            1330                1335

Leu Pro Leu Glu Glu Thr Glu Leu Glu Lys Arg Ile Ile Val Asp
1340            1345                1350

Asp Thr Ser Thr Gln Trp Ser Lys Asn Met Lys His Leu Thr Pro
1355            1360                1365

Ser Thr Leu Thr Gln Ile Asp Tyr Asn Glu Lys Glu Lys Gly Ala
1370            1375                1380

Ile Thr Gln Ser Pro Leu Ser Asp Cys Leu Thr Arg Ser His Ser
1385            1390                1395

Ile Pro Gln Ala Asn Arg Ser Pro Leu Pro Ile Ala Lys Val Ser
1400            1405                1410

Ser Phe Pro Ser Ile Arg Pro Ile Tyr Leu Thr Arg Val Leu Phe
1415            1420                1425

Gln Asp Asn Ser Ser His Leu Pro Ala Ala Ser Tyr Arg Lys Lys
1430            1435                1440

Asp Ser Gly Val Gln Glu Ser Ser His Phe Leu Gln Gly Ala Lys
1445            1450                1455

Lys Asn Asn Leu Ser Leu Ala Ile Leu Thr Leu Glu Met Thr Gly
1460            1465                1470

-continued

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His

-continued

|   |   |   |   |   | 1865 |   |   |   |   | 1870 |   |   |   |   | 1875 |   |
|---|---|---|---|---|---|---|---|---|---|---|---|---|---|---|---|---|

Thr Asn Thr Leu Asn Pro Ala His Gly Arg Gln Val Thr Val Gln
            1880                    1885                   1890

Glu Phe Ala Leu Phe Phe Thr Ile Phe Asp Glu Thr Lys Ser Trp
            1895                    1900                   1905

Tyr Phe Thr Glu Asn Met Glu Arg Asn Cys Arg Ala Pro Cys Asn
            1910                    1915                   1920

Ile Gln Met Glu Asp Pro Thr Phe Lys Glu Asn Tyr Arg Phe His
            1925                    1930                   1935

Ala Ile Asn Gly Tyr Ile Met Asp Thr Leu Pro Gly Leu Val Met
            1940                    1945                   1950

Ala Gln Asp Gln Arg Ile Arg Trp Tyr Leu Leu Ser Met Gly Ser
            1955                    1960                   1965

Asn Glu Asn Ile His Ser Ile His Phe Ser Gly His Val Phe Thr
            1970                    1975                   1980

Val Arg Lys Lys Glu Glu Tyr Lys Met Ala Leu Tyr Asn Leu Tyr
            1985                    1990                   1995

Pro Gly Val Phe Glu Thr Val Glu Met Leu Pro Ser Lys Ala Gly
            2000                    2005                   2010

Ile Trp Arg Val Glu Cys Leu Ile Gly Glu His Leu His Ala Gly
            2015                    2020                   2025

Met Ser Thr Leu Phe Leu Val Tyr Ser Asn Lys Cys Gln Thr Pro
            2030                    2035                   2040

Leu Gly Met Ala Ser Gly His Ile Arg Asp Phe Gln Ile Thr Ala
            2045                    2050                   2055

Ser Gly Gln Tyr Gly Gln Trp Ala Pro Lys Leu Ala Arg Leu His
            2060                    2065                   2070

Tyr Ser Gly Ser Ile Asn Ala Trp Ser Thr Lys Glu Pro Phe Ser
            2075                    2080                   2085

Trp Ile Lys Val Asp Leu Leu Ala Pro Met Ile Ile His Gly Ile
            2090                    2095                   2100

Lys Thr Gln Gly Ala Arg Gln Lys Phe Ser Ser Leu Tyr Ile Ser
            2105                    2110                   2115

Gln Phe Ile Ile Met Tyr Ser Leu Asp Gly Lys Lys Trp Gln Thr
            2120                    2125                   2130

Tyr Arg Gly Asn Ser Thr Gly Thr Leu Met Val Phe Phe Gly Asn
            2135                    2140                   2145

Val Asp Ser Ser Gly Ile Lys His Asn Ile Phe Asn Pro Pro Ile
            2150                    2155                   2160

Ile Ala Arg Tyr Ile Arg Leu His Pro Thr His Tyr Ser Ile Arg
            2165                    2170                   2175

Ser Thr Leu Arg Met Glu Leu Met Gly Cys Asp Leu Asn Ser Cys
            2180                    2185                   2190

Ser Met Pro Leu Gly Met Glu Ser Lys Ala Ile Ser Asp Ala Gln
            2195                    2200                   2205

Ile Thr Ala Ser Ser Tyr Phe Thr Asn Met Phe Ala Thr Trp Ser
            2210                    2215                   2220

Pro Ser Lys Ala Arg Leu His Leu Gln Gly Arg Ser Asn Ala Trp
            2225                    2230                   2235

Arg Pro Gln Val Asn Asn Pro Lys Glu Trp Leu Gln Val Asp Phe
            2240                    2245                   2250

Gln Lys Thr Met Lys Val Thr Gly Val Thr Thr Gln Gly Val Lys
            2255                    2260                   2265

```
-continued

Ser Leu Leu Thr Ser Met Tyr Val Lys Glu Phe Leu Ile Ser Ser
    2270            2275            2280

Ser Gln Asp Gly His Gln Trp Thr Leu Phe Phe Gln Asn Gly Lys
    2285            2290            2295

Val Lys Val Phe Gln Gly Asn Gln Asp Ser Phe Thr Pro Val Val
    2300            2305            2310

Asn Ser Leu Asp Pro Pro Leu Leu Thr Arg Tyr Leu Arg Ile His
    2315            2320            2325

Pro Gln Ser Trp Val His Gln Ile Ala Leu Arg Met Glu Val Leu
    2330            2335            2340

Gly Cys Glu Ala Gln Asp Leu Tyr
    2345            2350

<210> SEQ ID NO 12
<211> LENGTH: 24
<212> TYPE: DNA
<213> ORGANISM: Artificial
<220> FEATURE:
<223> OTHER INFORMATION: An artificially synthesized oligonucleotide
      sequence

<400> SEQUENCE: 12
caggggccag tggatagact gatg                                          24

<210> SEQ ID NO 13
<211> LENGTH: 23
<212> TYPE: DNA
<213> ORGANISM: Artificial
<220> FEATURE:
<223> OTHER INFORMATION: An artificially synthesized oligonucleotide
      sequence

<400> SEQUENCE: 13
gctcactgga tggtgggaag atg                                           23
```

BLOOD COAGULATION FACTOR VIII ACTIVATION-ENHANCING ANTIBODIES

TECHNICAL FIELD

The present invention relates to antibodies that enhance the generation of activated blood coagulation factor VIII, and pharmaceutical compositions using the antibodies.

BACKGROUND ART

Blood coagulation factor VIII which is absent or defective in patients with hemophilia A, a severe congenital bleeding disorder, functions as a cofactor in the Xase complex involved in the anionic phospholipid surface-dependent conversion of Factor X to Factor Xa by Factor IXa (Non-Patent Document 1). Factor VIII is protected and stabilized by vWF which circulates as a complex with this cofactor (Non-Patent Document 2). The factor is synthesized as a single-chain multidomain molecule (A1-A2-B-A3-C1-C2) consisting of 2,332 amino acid residues with a molecular weight up to 300 kDa (Non-Patent Documents 3 and 4), and processed into a series of metal ion-dependent heterodimers by cleavage at the B-A3 junction, generating a heavy chain consisting of the A1 and A2 domains, and heterogeneous fragments of partially proteolyzed B domains, and a light chain consisting of the A3, C1, and C2 domains that binds with the heavy chain (Non-Patent Documents 3 to 5).

Factor VIII is converted into activated blood coagulation factor VIII (also referred to as activated blood coagulation factor VIII or Factor VIIIa) by limited proteolysis with thrombin or Factor Xa (Non-Patent Document 6). Cleavage of the heavy chain at $Arg^{372}$ and $Arg^{740}$ generates 50-kDa A1 and 40-kDa A2 subunits. On the other hand, cleavage of the 80-kDa light chain at $Arg^{1689}$ generates a 70-kDa A3-C1-C2 subunit. Analyses of mutations and hemophilia A database suggest that proteolysis at the $Arg^{372}$ and $Arg^{1689}$ sites is essential for generating Factor VIIIa cofactor activity (Non-Patent Document 7). Cleavage at the former site exposes a functional Factor IXa-interactive site within the A2 domain which is cryptic in the inactivated molecule (Non-Patent Document 8). Meanwhile, cleavage at the latter site liberates the cofactor from its carrier protein, vWF, and contributes to the overall specific activity of the cofactor (Non-Patent Documents 9 and 10).

Serine proteases including activated protein C (APC), Factor Xa, Factor IXa, and plasmin inactivate Factor VIII (a) by cleavage at $Arg^{336}$ in the A1 domain. The inactivation by cleavage at $Arg^{336}$ can be associated with altered interaction between the A2 subunit and truncated A1, and the increase of $K_m$ for the substrate Factor X. The latter reflects the loss of a Factor X-interactive site within residues 337 to 372 of A1. Furthermore, Factor Xa and APC also attack the $Lys^{36}$ and $Arg^{562}$ sites, respectively. Cleavage at these sites has been suggested to change the structure of A1. The structural change of A1 limits its productive interaction with the A2 subunit, and impairs its bonding with Factor VIIIa A2 subunit and Factor IXa molecule in the Xase complex.

Factor VIII inhibitors are generated as isoantibodies in 20 to 30% of multi-transfused hemophilia A patients. Furthermore, autoantibodies can also arise in individuals who are originally normal.

In general, most of the Factor VIII inhibitor isoantibodies and autoantibodies that function as an anti-Factor VIII neutralizing antibody reduce or eliminate the Factor VIII activity. The Factor VIII-neutralizing mechanism of such antibodies has been intensively studied by various researchers. Antibodies that recognize one or more of the A2, C2, or A3-C1 epitopes block the binding of the Factor VIII molecule to some coagulation factors, for example, vWF (Non-Patent Documents 12 and 13), phospholipid (Non-Patent Documents 13 and 14), and Factor IXa (Non-Patent Documents 18 and 19). Furthermore, some of the antibodies inhibit the activation of Factor VIII mediated by thrombin (Non-Patent Document 14) or Factor Xa (Non-Patent Documents 15 and 16). Meanwhile, anti-Factor VIII antibodies that do not have the ability to neutralize Factor VIII activity have also been reported (namely, non-neutralizing antibodies) (Non-Patent Documents 20 and 21). Such antibodies in normal individuals or hemophilia A patients can be confirmed only by ELISA. However, most of the non-neutralizing antibodies are not expected to have any significant function, and the epitopes recognized by these antibodies remained unidentified.

Furthermore, for the treatment of blood coagulation-related diseases such as hemophilia A, it has been proposed to use antibodies that inhibit the binding between Factor VIII and low density lipoprotein receptor protein (LRP) which inactivates Factor VIII by binding to the A2 domain of activated blood coagulation factor VIII (Patent Document 1). In addition, antibodies that inhibit the reaction between Factor VIII and APC have been reportedly found in hemophilia A patients (Non-Patent Document 22). However, there is no known antibody to date that has the function of enhancing the activation of blood coagulation factor VIII.

[Patent Document 1] WO03/093313

[Non-Patent Document 1] Mann K. G., Nesheim M. E., Church W. R., Haley P., and Krishnaswamy S. (1990) Blood 76, 1-16

[Non-Patent Document 2] Hoyer L. W. (1981) Blood 58, 1-13

[Non-Patent Document 3] Wood W. I., Capon D. J., Simonsen C. C., Eaton D. L., Gitschier J., Keyt B., Seeburg P. H., Smith D. H., Hollingshead P., Wion K. L., Delwart E., Tuddenham E. D. G., Vehar G. A., and Lawn R. M. (1984) Nature 312, 330-7

[Non-Patent Document 4] Vehar G. A., Keyt B., Eaton D., Rodriguez H., O'Brien D. P., Rotblat F., Oppermann H., Keck R., Wood W. I., Harkins R. N., Tuddenham E. G. D., Lawn R. M., and Capon D. J. (1984) Nature 312, 337-42

[Non-Patent Document 5] Fay P. J., Anderson M. T., Chavin S. I., and Marder V. J. (1986) Biochim. Biophys. Acta 871, 268-78

[Non-Patent Document 6] Eaton D., Rodriguez H., and Vehar G. A. (1986) Biochemistry 25, 505-12

[Non-Patent Document 7] Fay P. J. (2004) Blood Rev. 18, 1-15

[Non-Patent Document 8] Fay P. J., Mastri M., Koszelak M. E., and Wakabayashi H. (2001) J. Biol. Chem. 276, 12434-9

[Non-Patent Document 9] Lollar P., Hill-Eubanks D. C., and Parker C. G. (1988) J. Biol. Chem. 263, 10451-5

[Non-Patent Document 10] Regan L. M., and Fay P. J. (1995) J. Biol. Chem. 270, 8546-52

[Non-Patent Document 11] Shima M. (2006) Int. J. Hematol. 83, 109-18

[Non-Patent Document 12] Shima M., Nakai H., Scandella D., Tanaka I., Sawamoto Y, Kamisue S., Morichika S., Murakami T., and Yoshioka A. (1995) Br. J. Haematol. 91, 714-21

[Non-Patent Document 13] Shima M., Scandella D., Yoshioka A., Nakai H., Tanaka I., Kamisue S., Terada S., and Fukui H. (1993) Thromb. Haemostasis 67, 240-6

[Non-Patent Document 14] Scandella D., Gilbert G. E., Shima M., Nakai H., Eagleson C., Felch M., Prescott R., Rajalakshmi K. J., Hoyer L. W., and Saenko E. (1995) Blood 86, 1811-9

[Non-Patent Document 15] Nogami K., Shima M., Hosokawa K., Nagata M., Koide T., Saenko E. L., Tanaka I., Shibata M., and Yoshioka A. (2000) J. Biol. Chem. 275, 25774-80

[Non-Patent Document 16] Nogami K., Shima M., Hosokawa K., Suzuki T., Koide T., Saenko E. L., Scandella D., Shibata M., Kamisue S., Tanaka I., and Yoshioka A. (1999) J. Biol. Chem. 274, 31000-7

[Non-Patent Document 17] Nogami K., Shima M., Nishiya K., Sakurai Y., Tanaka I., Giddings J. C., Saenko E. L., and Yoshioka A. (2002) Thromb. Haemostasis 87, 459-65

[Non-Patent Document 18] Fay P. J., and Scandella D. (1999) J. Biol. Chem. 274, 29826-30

[Non-Patent Document 19] Zhong D., Saenko E. L., Shima M., Felch M., and Scandella D. (1998) Blood 92, 136-42

[Non-Patent Document 20] Batle J., Gomez E., Rendal E., Torea J., Loures E., Couselo M., Vila P., Sedano C., Tusell X., Magallon M., Quintana M., Gonzalez-Boullosa R., and Lopes-Fernandez M. F. (1996) Ann Hematol 72, 321-6

[Non-Patent Document 21] Blanco A. N., Peirano A. A., Grosso S. H., Gennari L. C., Bianco R. P., and Lazzari M. A. (2000) Haematologica 85, 1045-50

[Non-Patent Document 22] Nogami K., Shima M., Giddings J. C., Hosokawa K., Nagata M., Kamisue S., Suzuki H, Shibata M., Saenko E. L., Tanaka I., and Yoshioka A. (2001) Blood 97, 669-77

DISCLOSURE OF THE INVENTION

Problems to be Solved by the Invention

An objective of the present invention is to provide effective means for preventing or treating diseases that develop or progress as a result of the decrease or loss of the blood coagulation factor VIII activity, for example, hemophilia A, acquired hemophilia, and von Willebrand's disease.

Means for Solving the Problems

After dedicated research, the present inventors discovered an anti-Factor VIII monoclonal antibody (named moAb216) that increases the coagulation-enhancing activity of Factor VIII to about 1.5 fold. The present inventors demonstrated that the moAb216-mediated increase of Factor VIII cofactor activity is due to change in the cleavage at $Arg^{372}$ and/or $Arg^{336}$ of the heavy chain of Factor VIII, which is induced by the interaction between the A2 domain and moAb216. moAb216 not only increases Factor VIII activity but also increases the generation of both Factor Xa and thrombin at a similar level.

moAb216 of the present invention recognizes the epitope in the A2 domain; however, it does not react with isolated A1 or the light chain subunit.

The moAb216-mediated enhancement of Factor VIII activity is a result of changes in the rate of proteolytic cleavage of the heavy chain by thrombin, Factor Xa, and APC. The formation of moAb216-Factor VIII complex accelerates the cleavage at $Arg^{372}$ in the A1-A2 domain junction of Factor VIII by thrombin and Factor Xa, both of which are representative Factor VIII activators, and decelerates the cleavage at $Arg^{336}$ in the A1 domain by APC, which is a representative Factor VIII inactivator. The cleavage at $Arg^{740}$ in the A2-B domain junction was however unaffected. These findings suggest that the molecular structure of Factor VIII which forms a complex with moAb216 is changed so that Factor VIII is cleaved more rapidly by thrombin or Factor Xa and more slowly by APC.

The moAb216 of the present invention is expected to provide a novel replacement therapy for hemophilia A patients. For example, based on the finding that the antibody enhances Factor VIII activity, intravenous administration of concentrates of recombinant Factor VIII complexed with moAb216 is expected to provide a higher level of Factor VIII activity with longer half-life as compared to when only recombinant Factor VIII is administered. The total dose of concentrated recombinant Factor VIII to be administered can be reduced by using such antibody. Furthermore, the effect of moAb216 in enhancing Factor VIII activity was also observed in the presence of Factor VIII inhibitors. In particular, the presence of A2 inhibitor had almost no influence on the antibody's effect of enhancing Factor VIII activity. Since most Factor VIII inhibitors recognize the A2 and/or C2 domain, moAb216 can be expected to provide a novel replacement therapy for congenital hemophilia A patients with isoantigen inhibitors or acquired hemophilia patients with autoantibodies.

Specifically, the present invention relates to the following inventions:

(1) an antibody that enhances the generation of activated blood coagulation factor VIII;

(2) the antibody of (1), wherein the generation of activated blood coagulation factor VIII is enhanced by enhancing the cleavage of blood coagulation factor VIII at the Arg of position 372;

(3) the antibody of (1) or (2), which recognizes the A2 domain of blood coagulation factor VIII;

(4) the antibody of any one of (1) to (3), which does not recognize the C2 region of blood coagulation factor VIII;

(5) the antibody of any one of (1) to (4), which further suppresses the inactivation of blood coagulation factor VIII;

(6) the antibody of (5), wherein the inactivation of activated blood coagulation factor VIII is suppressed by suppressing the cleavage at the Arg of position 336;

(7) the antibody of any one of (1) to (6), which comprises a complementarity determining region wherein the amino acid sequences of the H-chain CDR1, 2, and 3 comprise the amino acid sequences of SEQ ID NOs: 2, 3, and 4, respectively, or a complementarity determining region functionally equivalent thereto;

(8) the antibody of any one of (1) to (7), which comprises an H-chain variable region whose amino acid sequence is shown in SEQ ID NO: 1, or an H-chain variable region functionally equivalent thereto;

(9) the antibody of any one of (1) to (8), which comprises a complementarity determining region wherein the amino acid sequences of the L-chain CDR1, 2, and 3 comprise the amino acid sequences of SEQ ID NOs: 7, 8, and 9, respectively, or a complementarity determining region functionally equivalent thereto;

(10) the antibody of any one of (1) to (9), which comprises an L-chain variable region whose amino acid sequence is shown in SEQ ID NO: 6, or an L-chain variable region functionally equivalent thereto;

(11) an antibody that binds to the same epitope as the antibody of any one of (7) to (10);

(12) an antibody that inhibits binding of the antibody of any one of (7) to (10) to blood coagulation factor VIII in a competitive inhibition assay;

(13) a pharmaceutical composition comprising at least one antibody selected from (1) to (12) as an active ingredient;

(14) the pharmaceutical composition of (13), which is further used in combination with blood coagulation factor VIII;

(15) the pharmaceutical composition of (13) or (14), which is further used in combination with an antibody having the activity of suppressing the inactivation of activated blood coagulation factor VIII;

(16) the pharmaceutical composition of any one of (13) to (15), which is used to treat and/or prevent bleeding, a disease with bleeding, or a disease caused by bleeding;

(17) the pharmaceutical composition of (16), wherein the bleeding, disease with bleeding, or a disease caused by bleeding develops and/or progresses due to decrease or loss of the activity of blood coagulation factor VIII;

(18) the pharmaceutical composition of (17), wherein the disease that develops and/or progresses due to decrease or loss of the activity of blood coagulation factor VIII is hemophilia A;

(19) the pharmaceutical composition of (17), wherein the disease that develops and/or progresses due to decrease or loss of the activity of blood coagulation factor VIII is acquired hemophilia;

(20) the pharmaceutical composition of (17), wherein the disease that develops and/or progresses due to decrease or loss of the activity of blood coagulation factor VIII is von Willebrand's disease;

(21) a method for treating bleeding, a disease with bleeding, or a disease caused by bleeding, which comprises administering at least one antibody selected from (1) to (12), or any one of the pharmaceutical compositions of (13) to (20);

(22) use of at least one antibody selected from (1) to (12) in the manufacture of a pharmaceutical composition for preventing or treating bleeding, a disease with bleeding, or a disease caused by bleeding;

(23) the therapeutic method of (21), in which the bleeding, disease with bleeding, or disease caused by bleeding develops and/or progresses due to decrease or loss of the activity of blood coagulation factor VIII;

(24) the therapeutic method of (23), in which the disease that develops and/or progresses due to decrease or loss of the activity of blood coagulation factor VIII is hemophilia A;

(25) the therapeutic method of (23), in which the disease that develops and/or progresses due to decrease or loss of the activity of blood coagulation factor VIII is acquired hemophilia;

(26) the therapeutic method of (23), in which the disease that develops and/or progresses due to decrease or loss of the activity of blood coagulation factor VIII is von Willebrand's disease;

(27) the use of (22), in which the bleeding, disease with bleeding, or disease caused by bleeding develops and/or progresses due to decrease or loss of the activity of blood coagulation factor VIII;

(28) the use of (27), in which the disease that develops and/or progresses due to decrease or loss of the activity of blood coagulation factor VIII is hemophilia A;

(29) the use of (27), in which the disease that develops and/or progresses due to decrease or loss of the activity of blood coagulation factor VIII is acquired hemophilia; and

(30) the use of (27), in which the disease that develops and/or progresses due to decrease or loss of the activity of blood coagulation factor VIII is von Willebrand's disease.

Factor VIII (100 nM) was reacted with thrombin (1 nM) for the indicated time periods. The samples were electrophoresed on 8% gel, and then assayed by Western blotting using a biotinylated anti-A2 (JR8) monoclonal antibody. Panel c shows result of quantitative concentration measurement for the A2 subunit/A1-A2 subunit ratio obtained from the blotting data. The symbols used are: open circle, +moAb216; closed circle, −moAb216.

Figure 6A:
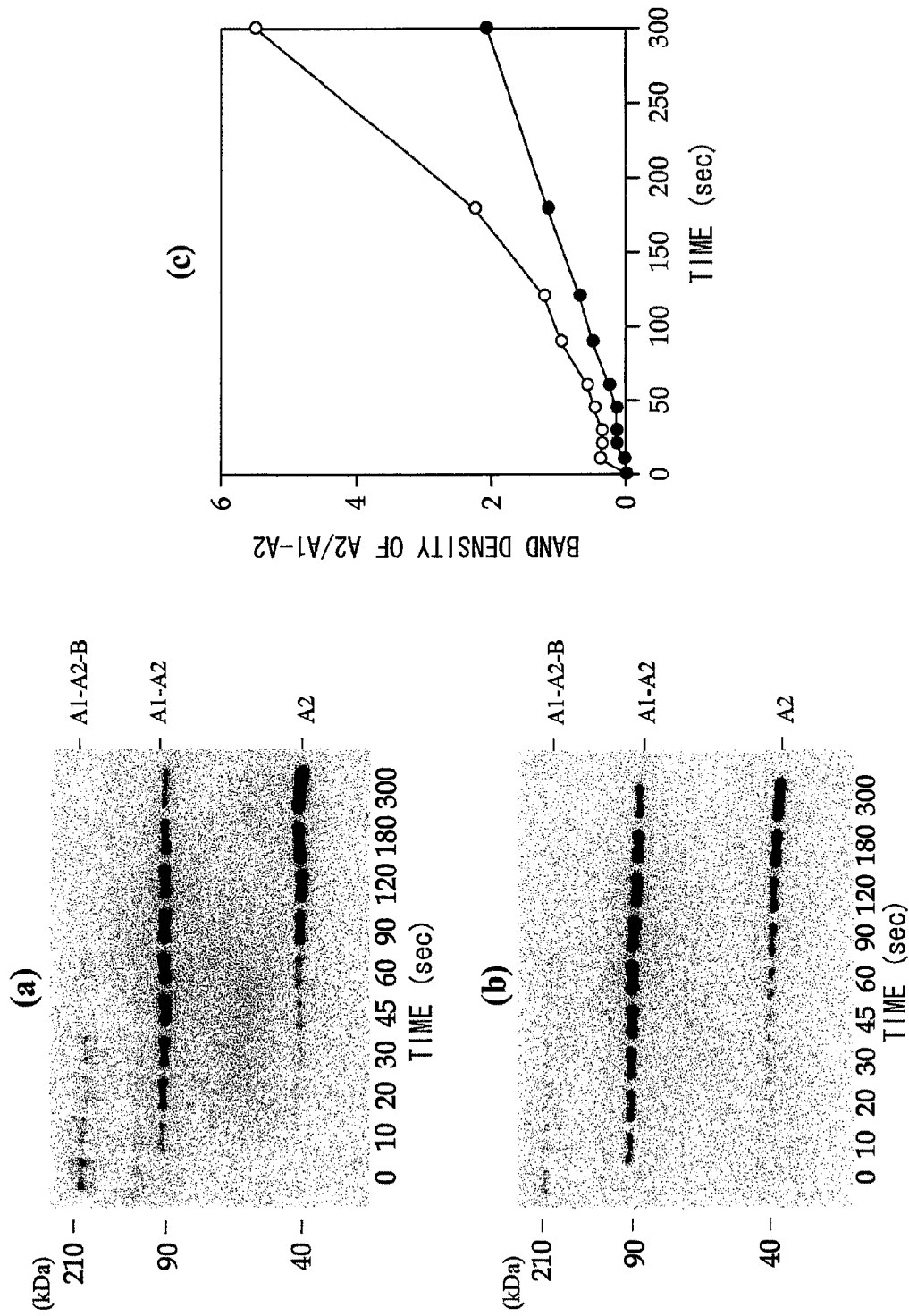
FIG. 6A shows the effect of moAb216 on the cleavage of Factor VIII heavy chain by thrombin, Factor Xa, or APC.
Figure 6B:
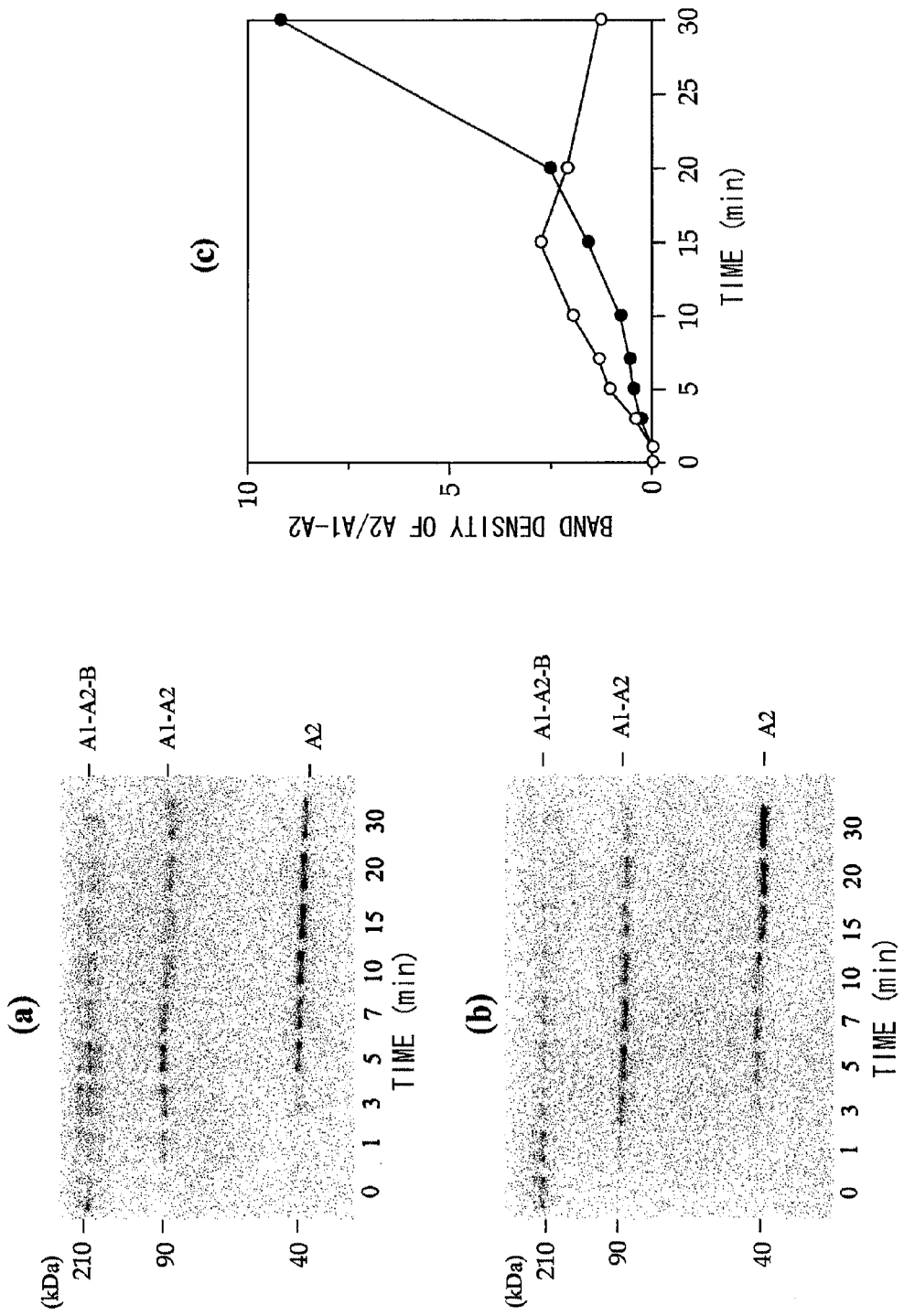

FIG. 6B shows the effect of moAb216 on the cleavage of Factor VIII heavy chain by thrombin, Factor Xa, or APC. Factor VIII (100 nM) was reacted with phospholipid (10 μM) and Factor Xa (4 nM) in the presence (Panel a) or absence (Panel b) of moAb216 (10 μg/ml) for the indicated time periods. The samples were electrophoresed on 8% gel, and then assayed by Western blotting using a biotinylated anti-A2 (JR8) monoclonal antibody. Panel c shows result of quantitative concentration measurement for the A2 subunit/A1-A2 subunit ratio obtained from the blotting data. The symbols used are: open circle, +moAb216; closed circle, −moAb216.

Figure 6C:
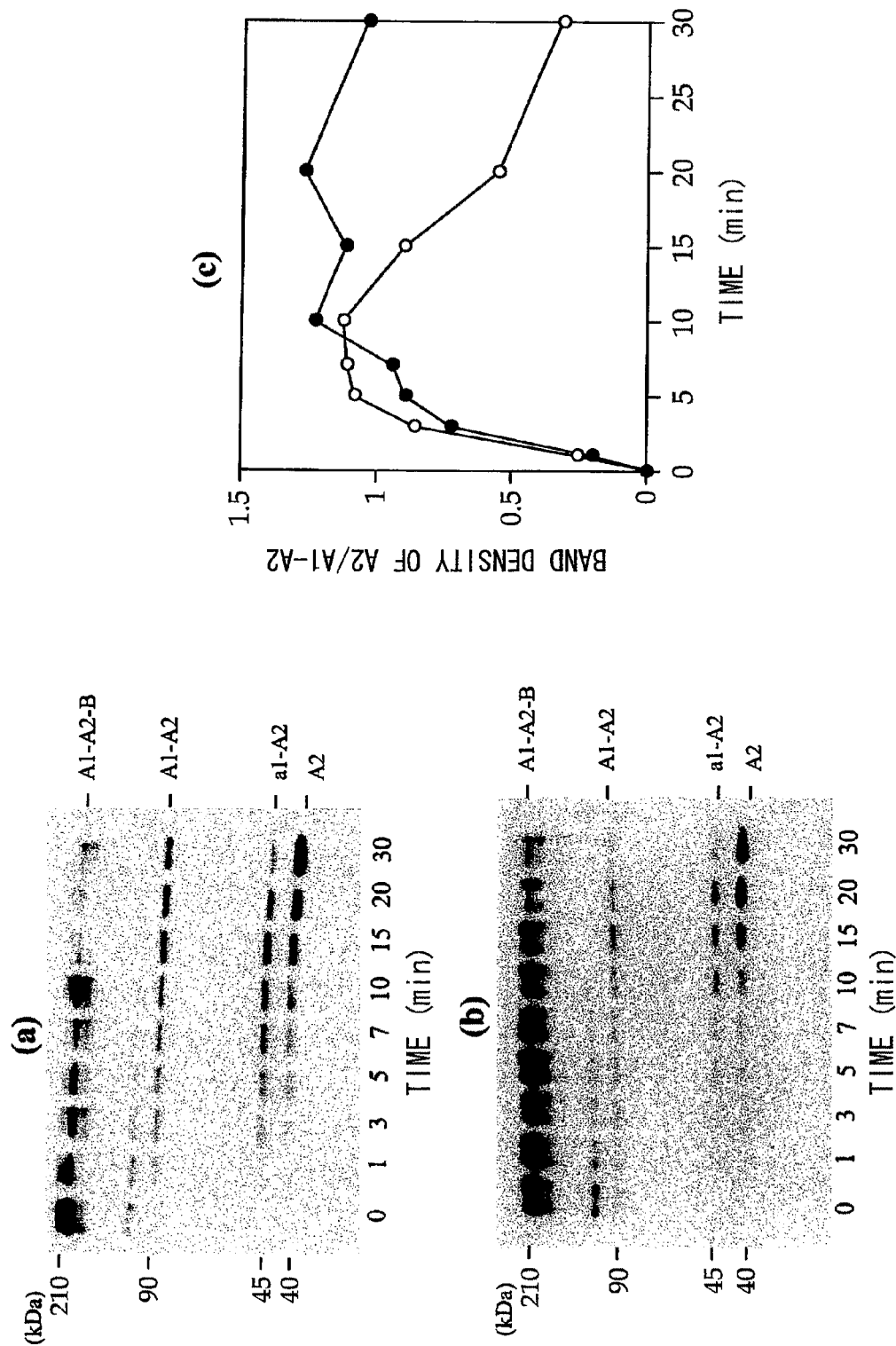

FIG. 6C shows the effect of moAb216 on the cleavage of Factor VIII heavy chain by thrombin, Factor Xa, or APC. Factor VIII (100 nM) was reacted with phospholipid (10 μM) and APC/protein S (40 nM/150 nM) in the presence (Panel a) or absence (Panel b) of moAb216 (10 μg/ml) for the indicated time periods. The samples were electrophoresed on 8% gel, and then assayed by Western blotting using a biotinylated anti-A2 (JR8) monoclonal antibody. Panel c shows result of quantitative concentration measurement for the a1-A2 subunit/A1-A2 subunit ratio obtained from the blotting data. The symbols used are: open circle, +moAb216; closed circle, −moAb216. a1 represents the acidic region (residues at positions 337 to 372) within the A1 domain.

Figure 7:
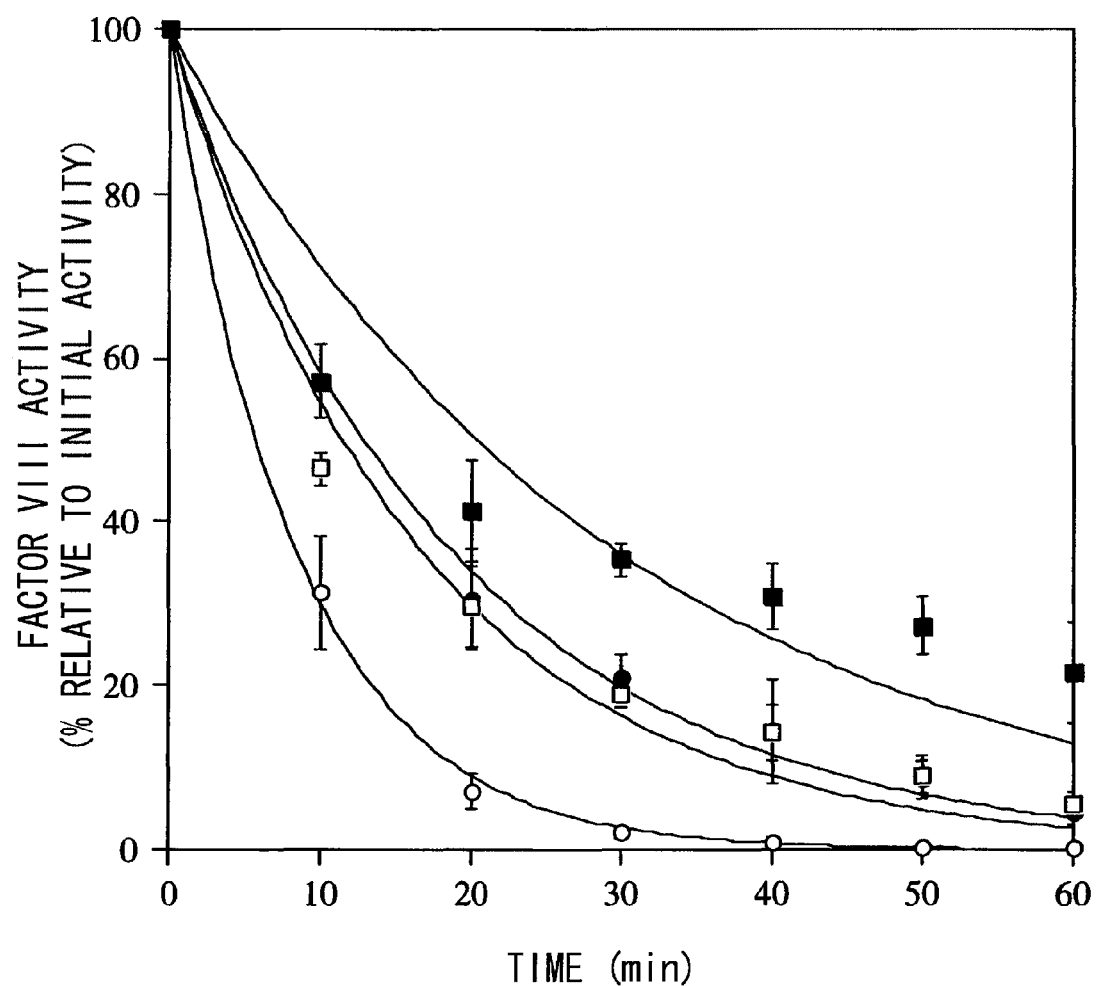

FIG. 7 shows the effect of moAb216 on the stability of Factor VIII protein. Factor VIII (circle, 0.4 nM) or normal plasma (square) was incubated in the absence (open symbols) or presence (closed symbols) of moAb216 (50 μg/ml) at 55° C. Aliquots were sampled at the indicated time points, and their activities were assayed. The data was analyzed using exponential decay formula (Formula 1).

BEST MODE FOR CARRYING OUT THE INVENTION

Antibodies of the present invention enhance the generation of activated blood coagulation factor VIII. The antibodies of the present invention may be an antibody fragment or modified antibody. Such antibody fragments include diabody (Db), linear antibody, and single-chain antibody (herein also referred to as scFv) molecules. Herein, the "Fv" fragment is a minimal antibody fragment containing the complete antigen recognition and binding sites. "Fv" is a dimer ($V_H$-$V_L$ dimer) composed of one heavy (H) chain variable region ($V_H$) and one light (L) chain variable region ($V_L$) bound strongly by non-covalent bonding. An antigen binding site is formed on the surface of the $V_H$-$V_L$ dimer through interactions between the three complementarity determining regions (CDRs) of each variable region. Six CDRs form the antigen binding site of an antibody. However, even one variable region (i.e., half of an Fv containing only three antigen-specific CDRs) has the ability to recognize and bind to an antigen, although its affinity is lower than that of the complete binding site. Thus, fragments containing only one variable region or CDR, and half Fv containing only three CDRs are also included in the antibodies of the present invention, as long as they have the activity of enhancing the generation of activated blood coagulation factor VIII.

An Fab fragment (also referred to as F(ab)) further contains an L-chain constant region and an H-chain constant region (CH1). An Fab' fragment differs from an Fab fragment in that it has several additional residues derived from the carboxyl end of the H-chain CH1 region which contains one or more cysteines from the hinge domain of an antibody. Fab'-SH refers to Fab' that has free thiol-group in one or more cysteine residues in the constant region. An F(ab') fragment is produced by cleavage of the disulfide bonds between cysteines in the hinge region of the F(ab')$_2$ pepsin digest. Other chemically linked antibody fragments known to those skilled in art are also included in the antibody of the present invention.

A diabody refers to a bivalent antibody fragment constructed by gene fusion (Holliger P et al., Proc. Natl. Acad. Sci. USA 90: 6444-6448 (1993); EP 404,097; WO93/11161 and such). Diabodies are dimers composed of two polypeptide chains, and in each polypeptide chain, an L-chain variable region ($V_L$) and an H-chain variable region ($V_H$) are linked via a linker short enough, for example, a linker of about five amino acids, within the same chain that they cannot bind to each other. The $V_L$ and $V_H$ domains encoded by a same polypeptide chain form a dimer because the linker between $V_L$ and $V_H$ is too short to form a single-chain variable region fragment. Therefore, a diabody contains two antigen-binding sites.

Single-chain antibodies and scFv antibody fragments contain antibody $V_H$ and $V_L$ regions, and these regions exist within a single polypeptide chain. In general, Fv polypeptides further contain a polypeptide linker between $V_H$ and $V_L$ regions. Thus, scFv is able to form a structure required for antigen binding (as a review on scFv, see Pluckthun "The Pharmacology of Monoclonal Antibodies" Vol. 113 (Rosenburg and Moore ed. (Springer Verlag, New York) pp. 269-315, 1994)). The linker of the present invention is not particularly limited, as long as it does not inhibit the expression and activity of antibody variable regions linked at its two ends.

Furthermore, if needed, the antibodies of the present invention may be bispecific antibodies. IgG-type bispecific antibodies can be secreted from hybrid hybridomas (quadromas), which are generated by fusing two types of IgG antibody-producing hybridomas (Milstein C et al., Nature 1983, 305: 537-540). Alternatively, bispecific antibodies can be secreted by introducing into cells genes of the L chains and H chains constituting two types of IgGs of interest and coexpressing a total of four genes. If needed, IgG with a heterologous combination of H chains can be preferentially secreted by introducing appropriate amino acid substitutions into the H-chain CH3 region (Ridgway J B et al., Protein Engineering 1996, 9: 617-621; Merchant A M et al., Nature Biotechnology 1998, 16: 677-681).

Alternatively, bispecific antibodies can be prepared by chemically crosslinking Fab'. Bispecific F(ab')$_2$ can be prepared by crosslinking two Fab' derived from different antibodies, for example, by maleimidating Fab' prepared from one antibody with ortho-phenylenedimaleimide (o-PDM) and then reacting it with Fab' prepared from the other antibody (Keler T et al., Cancer Research 1997, 57: 4008-4014). Furthermore, there are known methods for chemically linking antibody fragments such as Fab'-thionitrobenzoic acid (TNB) derivatives and Fab'-thiol (SH) (Brennan M et al., Science 1985, 229: 81-83).

Leucine zippers, such as those derived from Fos and Jun, may be used instead of chemical crosslinks. This takes advantage of the fact that Fos and Jun prefer to form heterodimers although they form homodimers too. Fab' attached to Fos-derived leucine zipper and Fab' attached to Jun-derived leucine zipper are expressed. Bispecific F(ab')$_2$ can be prepared by mixing and reacting monomers of Fab'-Fos and Fab'-Jun reduced under a mild condition (Kostelny S A et al., J. of Immunology, 1992, 148: 1547-53). This method is not limited to Fab' and can also be applied when linking scFv, Fv, or such.

Diabodies can also be prepared to have bispecificity. Bispecific diabodies are heterodimers of two cross-over scFv fragments. Specifically, bispecific diabodies can be obtained by preparing a heterodimer composed of $V_H(A)-V_L(B)$ and $V_H(B)-V_L(A)$, both of which are produced by linking $V_H$ and $V_L$ derived from two types of antibodies A and B, via a relatively short linker of about five residues (Holliger P et al., Proc of the National Academy of Sciences of the USA 1993, 90: 6444-6448).

Alternatively, the target configuration can be enhanced by linking two types of scFv via a relatively long, flexible linker of about 15 residues (single-chain diabody; Kipriyanov S M et al., J of Molecular Biology. 1999, 293: 41-56) or by appropriate amino acid substitution (knobs-into-holes: Zhu Z et al., Protein Science. 1997, 6: 781-788).

sc $(Fv)_2$ prepared by linking two types of scFv via a relatively long, flexible linker of about 15 residues can also be bispecific antibodies (Mallender W D et al., J of Biological Chemistry, 1994, 269: 199-206).

The antibody of the present invention also includes modified antibodies. Such modified antibodies include, for example, antibodies conjugated with various molecules such as polyethylene glycol (PEG). There is no limitation to the substances used for conjugation with the modified antibodies of the present invention, and antibodies can be modified for various purposes, such as to stabilize antibodies or enhance binding activity. Such modified antibodies can be obtained by chemically modifying the antibodies prepared, and these methods are already established in the art.

The origin of antibodies of the present invention is not limited. The antibodies may be human, mouse, or rat antibodies. In addition, the antibodies may be genetically altered antibodies, such as chimeric or humanized antibodies.

Methods for obtaining human antibodies are already known. For example, human antibodies of interest can be obtained by using an antigen of interest to immunize transgenic animals that have the entire repertoire of human antibody genes (see WO 93/12227, WO 92/03918, WO 94/02602, WO 94/25585, WO 96/34096, and WO 96/33735).

Genetically altered antibodies can be produced by known methods. Specifically, for example, chimeric antibodies comprise the H-chain and L-chain variable regions of an antibody from an immunized animal, and the H-chain and L-chain constant regions of a human antibody. Chimeric antibodies can be obtained by ligating DNAs that encode the variable regions of an antibody derived from an immunized animal with DNAs encoding the constant regions of a human antibody, inserting the ligated DNA into an expression vector, and then introducing the construct into a host to produce the antibody.

A humanized antibody, which is also called a reshaped human antibody, is an altered antibody. Humanized antibodies can be constructed by grafting the CDR of an antibody derived from an immunized animal to the complementarity determining region of a human antibody. General genetic recombination techniques for preparing such antibodies are also known.

Specifically, a DNA sequence designed to ligate a mouse antibody CDR with the framework region (FR) of a human antibody is synthesized by PCR using several oligonucleotides constructed to contain overlapping portions at their ends. A humanized antibody can be obtained by: (1) ligating the obtained DNA to a DNA that encodes a human antibody constant region; (2) inserting the resulting construct into an expression vector; and (3) introducing the vector into a host to produce the antibody (see European Patent Application No. EP 239,400, and International Patent Application No. WO 96/02576). Human antibody FRs linked via the CDR are selected so that the complementarity determining region forms a favorable antigen-binding site. If needed, amino acids in the framework region of an antibody variable region may be substituted such that the CDR of a reshaped human antibody forms an appropriate antigen-binding site (Sato K et al, Cancer Research 1993, 53: 851-856). Alternatively, the framework regions may be substituted by various framework regions derived from human antibodies (see International Patent Application WO 99/51743).

The present invention relates to antibodies that enhance the generation of activated blood coagulation factor VIII. Activated blood coagulation factor VIII is activated via cleavage at the arginine (Arg) of position 372 by thrombin or Factor Xa. Thus, the present invention relates to antibodies that enhance the cleavage at the arginine of position 372.

Meanwhile, blood coagulation factor VIII is inactivated via cleavage of A1 domain at the Arg of position 336 by APC. Accordingly, the enhancement of the generation of activated blood coagulation factor VIII mediated by an antibody of the present invention may be achieved through suppression of the inactivation of blood coagulation factor VIII. Thus, the preferred antibodies of the present invention include antibodies that suppress the cleavage of blood coagulation factor VIII at the Arg of position 336.

Furthermore, the present invention demonstrated that antibodies that recognize and bind to the A2 domain altered the above-described cleavages of Factor VIII heavy chain at $Arg^{372}$ and/or $Arg^{336}$. Changes in the cleavage associated with activation or inactivation by the antibody of the present invention do not involve the C2 domain of Factor VIII. Thus, the preferred antibodies of the present invention include antibodies that recognize the A2 domain of blood coagulation factor VIII and antibodies that do not recognize the C2 domain.

Methods for obtaining the antibodies of the present invention are not particularly limited, and the antibodies may be obtained by any method. For example, antibodies can be prepared by immunizing animals with an antigen. Animals used for immunization include, for example, mice, hamsters, and Rhesus monkeys. These animals can be immunized with antigens using methods well known to those skilled in the art.

Antigens used for immunizing animals include complete antigens with immunogenicity, and incomplete antigens (including haptens) without immunogenicity. In the present invention, for example, human Factor VIII is used as the antigen (immunogen) described above. Human Factor VIII is public knowledge, and the protein can be purified by known methods and used as antigen. Furthermore, the amino acid sequence of human Factor VIII is also public knowledge (SEQ ID NO: 11; GenBank Accession No. NP_000123), and thus the protein or a portion thereof can be produced based on the known sequence using genetic recombination techniques and used as antigen. The factor used as immunogen may be a whole protein that constitutes the factor or a partial peptide of the protein. In some cases, the immunogen used for immunizing animals may be a soluble antigen prepared by linking the antigen to another molecule; and in some cases, their fragments may be used as necessary. Alternatively, cells expressing the antigen on the cell surface can be used as immunogen if needed. Such cells may be natural cells (tumor cell lines and the like) or cells constructed by genetic recombination techniques to express the antigen molecule.

Animals are immunized with sensitizing antigens using known methods, for example, the methods described in the Examples. Common methods include intraperitoneal or subcutaneous injection of a sensitizing antigen into mammals. Specifically, a sensitizing antigen is suspended and diluted with an appropriate amount of PBS, physiological saline, or such. An appropriate amount of a standard adjuvant, for example, Freund's complete adjuvant, is combined with the suspension if required, and the mixture is emulsified. Then, the emulsion is administered to mammals several times over a 4- to 21-day interval. Appropriate carriers may be used when immunizing a sensitizing antigen. After a mammal is immunized as described above, and elevation of the level of the desired antibody in the serum is confirmed, immune cells are collected from the mammal and subjected to cell fusion.

Herein, preferable immune cells include, particularly, spleen cells. In general, mammalian myeloma cells are used as parental cells for fusion with the immune cells. Various myeloma cell lines are known, and any of them can be used. Those preferably used include, for example, P3 (P3x63Ag8.653) (J. Immunol. (1979) 123: 1548-50), P3x63Ag8U.1 (Curr. Topics Microbiol. Immunol. (1978) 81: 1-7), NS-1 (Kohler and Milstein, Eur. J. Immunol. (1976) 6: 511-9), MPC-11 (Margulies et al., Cell (1976) 8: 405-15), SP2/0 (Shulman et al., Nature (1978) 276: 269-70), F0 (deSt. Groth et al., J. Immunol. Methods (1980) 35: 1-21), S194 (Trowbridge, J. Exp. Med. (1978) 148: 313-23), and R210 (Galfre et al., Nature (1979) 277: 131-3). Essentially, the above immune cells can be fused with myeloma cells according to known methods, for example, the method of Kohler and Milstein (Kohler and Milstein, Methods Enzymol. (1981) 73:3-46).

More specifically, cell fusion can be carried out, for example, in a conventional culture medium in the presence of a cell fusion-enhancing agent. For example, polyethylene glycol (PEG), hemagglutinating virus of Japan (HVJ), or such can be used as the fusion-enhancing agent. If required, an adjuvant such as dimethylsulfoxide can be added to improve fusion efficiency. The ratio of immune cells to myeloma cells can be appropriately determined. In general, for example, it is preferable to use 1 to 10 immune cells for each myeloma cell. Culture media used in cell fusions include, for example, RPMI1640 and MEM, which are suitable for growing myeloma cell lines. Culture media generally used for these types of cell cultures can also be suitably used. Furthermore, serum supplements such as fetal calf serum (FCS) may be added to culture media. Cell fusion can be carried out by the following procedure: mixing immune cells well with a specified quantity of myeloma cells in a culture medium; pre-warming a PEG (for example, average molecular weight of about 1000 to 6000) solution to about 37° C.; adding the PEG solution at a concentration of 30% to 60% (w/v); and then mixing the combined solution to generate fused cells (hybridomas) of interest. Next, to remove cell fusion agents and the like, which are unfavorable to hybridoma growth, the following steps are repeated: adding an appropriate culture medium sequentially; centrifuging the mixture; and removing the supernatant. Hybridoma selection can be achieved by culturing the generated hybridomas in a conventional selection medium, for example, HAT medium (a culture medium containing hypoxanthine, aminopterin, and thymidine). Culture is continued using the above-described HAT medium for a sufficient period of time (typically, several days to several weeks) to kill cells (non-fused cells) other than the hybridomas of interest. The hybridomas are then screened and hybridomas producing desired antibodies are cloned into single clones according to conventional limiting dilution methods.

Alternatively, instead of obtaining hybridomas by immunizing nonhuman animals with an antigen by the procedures described above, hybridomas producing the desired human antibody can be obtained by sensitizing human lymphocytes with an antigen in vitro and fusing the sensitized lymphocytes with human myeloma cells that are capable of perpetual division (see Japanese Patent Application Kokoku Publication No. (JP-B) H1-59878 (examined, approved Japanese patent application published for opposition). Alternatively, hybridomas producing the desired human antibody may be obtained by administering an antigen to transgenic animals that have the entire repertoire of human antibody genes to produce antibody-producing cells, and then immortalizing them (see International Patent Application WO 94/25585, WO 93/12227, WO92/03918, and WO 94/02602).

Monoclonal antibody-producing hybridomas prepared as above can be passaged in conventional culture media and stored in liquid nitrogen for long periods.

Methods for obtaining monoclonal antibodies from hybridomas include a method of obtaining monoclonal antibodies as culture supernatants of hybridomas cultured by conventional methods. Alternatively, a method of administering hybridomas to a mammal compatible with the hybridomas, allowing the cells to grow, and obtaining monoclonal antibodies from ascites of the animal. The former method is suitable for preparing high purity antibodies, and the latter is suitable for large scale production of antibodies.

Antibodies of the present invention can also be prepared as recombinant antibodies by using genetic recombination techniques to clone antibody genes from hybridomas, insert the genes into appropriate vectors, and introduce the resulting vectors into hosts (see, for example, Vandamme et al., Eur. J. Biochem. (1990) 192:767-75). Specifically, an mRNA encoding the variable (V) region is first isolated from hybridomas producing an antibody of interest. The mRNA can be isolated by the following procedure. Total RNA is prepared from antibody-producing spleen cells by known methods, for example, guanidine-ultracentrifugation methods (Chirgwin et al., Biochemistry (1979) 18:5294-9) and AGPC methods (Chomczynski et al., Anal. Biochem. (1987) 162:156-9), and then a desired mRNA is prepared using an mRNA purification kit (Pharmacia) or such. Alternatively, it is possible to directly prepare just the mRNA by using the QuickPrep mRNA Purification Kit (Pharmacia). Then, cDNA for the antibody V region is synthesized from the obtained mRNA using reverse transcriptase. cDNA synthesis can be carried out using the AMV Reverse Transcriptase First-strand cDNA Synthesis Kit (Seikagaku Co.) or such. Alternatively, cDNA can be synthesized and amplified by PCR-based 5'-RACE (Frohman et al., Proc. Natl. Acad. Sci. USA (1988) 85:8998-9002; Belyavsky et al., Nucleic Acids Res. (1989) 17:2919-32) using a 5'-Ampli FINDER RACE Kit (Clontech) or such. For example, cDNAs of the L-chain and H-chain variable regions are yielded by RT-PCR using primers corresponding to sites adjacent to the variable regions. It is possible to use primers corresponding to the CDRs, primers corresponding to the frameworks which are less diverse than the CDRs, and primers corresponding to the signal sequence and CH1 or L-chain constant region ($C_L$). Then, a DNA fragment of interest is purified from the obtained PCR product and ligated with a vector DNA to prepare a recombinant vector. The recombinant vector is then introduced into a host such as E. coli, and colonies of transformed cells are selected. The desired recombinant antibody can be produced by culturing the prepared cells. If required, the nucleotide sequence of a gene encoding the protein of interest is determined by known methods, for example, dideoxynucleotide methods. Then, the obtained DNA which encodes the V region of the antibody of interest is inserted into an expression vector that carries a DNA encoding a desired antibody constant region (C region). The expression vector has an expression regulatory region, for example, an enhancer and promoter. The antibody DNA is inserted into the expression vector so that the antibody of the present invention is expressed under the regulation of the expression regulatory region. Then, the desired antibody is expressed and prepared using appropriate host cells transformed with the expression vector.

To express an antibody gene, DNAs encoding an antibody heavy chain (H chain) and light chain (L chain) may be separately inserted into different expression vectors and host cells may be co-transformed with these vectors, or host cells may be transformed with a single expression vector carrying both an H-chain encoding DNA and an L-chain encoding DNA (see WO 94/11523).

The obtained antibody can be purified to homogeneity. Antibodies can be separated and purified by conventional methods for protein separation and purification. For example, antibodies can be separated and purified by appropriately selecting or combining methods that include, but are not limited to, chromatographic columns for affinity chromatography or such, filtration, ultrafiltration, salting out, dialysis, SDS-polyacrylamide gel electrophoresis, and isoelectric focusing (Antibodies: A Laboratory Manual. Ed Harlow and David Lane, Cold Spring Harbor Laboratory, 1988). Columns for affinity chromatography include protein A columns and protein G columns.

In the present invention, antibodies that have the activity of enhancing the generation of activated blood coagulation factor VIII can be selected, for example, by incubating antibodies with Factor VIII and assaying the activity of Factor VIII, according to the description of (3) Coagulation assay, "Materials and Methods" in the Examples.

In the present invention, an anti-Factor VIII monoclonal antibody that increases the coagulation-enhancing activity of Factor VIII up to about 1.5 fold was obtained. The antibody was named moAb216. The H-chain and L-chain variable regions of the antibody consist of the sequences shown in SEQ ID NOs: 1 and 6, respectively. The antibody can be obtained, for example, by the following procedure: inserting the variable regions into a single expression vector or separate expression vectors carrying $C_L$ and $C_H$; and introducing the vectors into host cells to express the antibody. The preferred antibody of the present invention includes, for example, moAb216, but is not limited thereto. Furthermore, the antibody of the present invention also includes antibodies that recognize the site recognized by moAb216 in blood coagulation factor VIII. In addition, the antibody of the present invention also includes antibodies comprising the same or functionally equivalent amino acid sequence as moAb216.

Herein, "functionally equivalent" means that an antibody of interest has the same biological or biochemical activity as the antibody of the present invention. Such biological or biochemical activities of antibody include, for example, binding activities and agonistic activities. Specifically, whether an antibody of interest is functionally equivalent to the antibody of the present invention can be examined by measuring the activity of the antibody of interest to enhance the generation of activated blood coagulation factor VIII.

Such functionally equivalent antibodies include, for example, antibodies having high homology to moAb216. In general, high homology means an amino acid identity of at least 50% or more, preferably 75% or more, more preferably 85% or more, and still more preferably 95% or more. Polypeptide homology can be determined, for example, by using algorithms described in the references (Wilbur and Lipman, Proc. Natl. Acad. Sci. USA (1983) 80: 726-30). Such functionally equivalent homologous antibodies in the present invention can be obtained, for example, through hybridization, gene amplification, or such using probes or primers prepared based on the sequence information of DNAs encoding the antibodies of the present invention. Target samples of hybridization or gene amplification include cDNA libraries constructed from cells that are anticipated to express such antibodies.

The antibodies of the present invention also include antibodies that are obtained as described above and whose amino acid sequences are altered by amino acid substitutions, deletions, additions, and/or insertions, or such. Such amino acid alterations can be performed by known methods.

The antibodies of the present invention include antibodies comprising any of the variable regions of moAb216, but are not particularly limited thereto. H chain is more important for antigen specificity than L chain. This is obvious from the finding that the L chain of antibodies against various antigens are identical, which is described, for example, in Nature Biotechnology, vol. 16, 677, 1998. Thus, the antibodies of the present invention preferably include antibodies comprising a complementarity determining region whose H-chain CDR1, 2, and 3 comprise the amino acid sequences of SEQ ID NOs: 2, 3, and 4, respectively, or a complementarity determining region functionally equivalent thereto. More preferably, the antibodies of the present invention include antibodies comprising an H chain whose variable region comprises the amino acid sequence of SEQ ID NO: 1, or an H chain functionally equivalent thereto. The amino acid sequences of the L-chain CDR1, 2, and 3 of moAb216 are shown in SEQ ID NOs: 7, 8, and 9, respectively. Thus, the antibodies of the present invention include antibodies comprising a complementarity determining region whose L-chain CDR1, 2, and 3 comprise the amino acid sequences of SEQ ID NOs: 7, 8, and 9, respectively, or a complementarity determining region functionally equivalent thereto. More preferably, the antibodies of the present invention include antibodies comprising an L chain whose variable region comprises the amino acid sequence of SEQ ID NO: 6, or an L chain functionally equivalent thereto.

The antibodies of the present invention include antibodies that bind to the same epitope as an antibody that comprises either variable region of moAb216 in a competitive inhibition assay, and antibodies that inhibit the binding of blood coagulation factor VIII and antibodies that comprise either variable region of moAb216, but are not particularly limited thereto. Competitive binding assays can be measured according to known methods, for example, solid-phase direct or indirect radioimmunoassay (RIA), solid phase direct or indirect enzyme immunoassay (EIA), sandwich competition assay (Stahli et al., Methods in Enzymology 9:242-253 (1983)), solid phase direct biotin-avidin EIA (Kirkland et al., J. Immunol. 137:3614-3619 (1986)), solid phase direct labeled assay, solid phase direct labeled sandwich assay (Harlow and Lane, "Antibodies, A Laboratory Manual" Cold Spring Harbor (1988)), solid phase direct label RIA (Morel et al., Molec. Immunol. 25(1):7-15 (1988)), solid phase direct biotin-avidin EIA (Cheung et al., Virology 176:546-552 (1990)), and direct labeled RIA (Moldenhauer et al., Scand. J. Immunol. 32:77-82 (1990)). Specifically, for example, a mixture of labeled moAb216 and the antibody to be detected is incubated in the presence of blood coagulation factor VIII, and the binding of labeled moAb216 and Factor VIII is detected. More specifically, for example, using a method similar to Example (6) described below, inhibition of the binding of an antibody comprising either variable region of moAb216 to blood coagulation factor VIII can be measured.

Since antibodies of the present invention enhance the generation of activated blood coagulation factor VIII, they are expected to serve as effective agents for bleeding, diseases with bleeding, or diseases caused by bleeding.

Decrease or loss of the function of Factor VIII/Factor VIIIa (hereinafter "F.VIII/F.VIIIa"), Factor IX/Factor IXa, or Factor XI/Factor XIa is known to cause a bleeding disorder called hemophilia. Among hemophilias, a congenital bleeding disorder caused by the decrease or loss of the function of F.VIII/F.VIIIa is called hemophilia A. When patients with hemophilia A bleed, they are treated by replacement therapy with F.VIII agents. Furthermore, on the days of vigorous workout/hiking, in cases of severe hemophilia and/or when joint bleeding is frequently repeated, F.VIII agents are sometimes administered preventively (see Non-Patent Documents 2 and 3). In recent years, the prophylactic administration of F.VIII agents is becoming very popular for substantially reducing bleeding episodes in hemophilia A patients. The reduction of bleeding episodes not only reduces lethal and nonlethal bleeding risks and the accompanying distresses, but also prevents hemophilic arthropathy caused by frequent joint bleeding. Thus, it greatly contributes to the improvement of quality of life in hemophilia A patients.

The half-life of F.VIII preparation in blood is about 12 to 16 hours, which is short. Accordingly, F.VIII agents need to be administered about three times a week for continuous prevention. This corresponds to maintenance of about 1% or more F.VIII activity (see Non-Patent Documents 4 and 5). Furthermore, in cases of bleeding except for mild hemorrhage, it is necessary to regularly administer F.VIII agents in substitution therapy for a certain period of time to completely arrest bleeding and prevent recurrent bleeding.

F.VIII agents are administered intravenously. There are technical difficulties associated with intravenous administration. In particular, intravenous administration in junior patients is more difficult because of their thinner veins.

In most cases of the preventive administration of F.VIII agents described above or emergency administration after bleeding, home care therapy and/or self-injection is employed. The need for frequent administration and technical difficulty not only cause distress to patients at the time of administration, but also become impeding factors of the prevalence of self-injection and/or home care therapy. Thus, there have been strong demands for agents that can be administered at longer intervals or by simpler methods when compared to conventional blood coagulation factor VIII agents.

Furthermore, hemophilia A patients, in particular, patients with severe hemophilia A may produce anti-F.VIII antibodies in themselves that are referred to as inhibitors. If an inhibitor is generated, the effects of an F.VIII preparation are inhibited by the inhibitor. As a result, hemostatic control becomes very difficult for patients.

Bleeding in such hemophilia A inhibitor patients is in general treated by neutralization therapy using a large amount of F.VIII agent or bypass therapy using a complex concentrate or F.VIIa agent. However, in neutralization therapy, the administration of a large amount of F.VIII agent may adversely increase the inhibitor (anti-F.VIII antibody) titer. In bypass therapy, the short blood half-life of complex concentrates and F.VIIa agent (about 2 to 8 hours) is problematic. In addition, since their action mechanisms are independent of the function of F.VIII/F.VIIIa, in other words, the function to catalyze F.IXa-mediated F.X activation, the hemostatic mechanism sometimes may not function properly and become nonresponsive. Therefore, when compared to hemophilia A non-inhibitor patients, sufficient hemostatic effect is not obtained in many cases of hemophilia A inhibitor patients. Thus, there have been strong demands for agents that substitute for the function of F.VIII/F.VIIIa and which are not affected by the presence of the inhibitor.

In addition to hemophilia and acquired hemophilia with anti-F.VIII autoantibodies, bleeding disorders associated with F.VIII/F.VIIIa also include von Willebrand's disease. von Willebrand's disease is known to be caused by functional abnormality or deficiency of vWF. vWF is necessary not only for the normal adhesion of platelets to subendothelial tissues at sites of vessel wall damage, but also for the formation of complex with F.VIII to maintain a normal plasma F.VIII level. In patients with von Willebrand's disease, these functions are depressed and functional abnormality of hemostasis occurs.

Antibody-based methods are considered when creating pharmaceuticals that: (i) have long administration intervals; (ii) are easily administered; (iii) are unaffected by the presence of inhibitors; and (iv) can functionally substitute for F.VIII/F.VIIIa in an F.VIII/F.VIIIa-independent manner. The half-life of antibodies in blood is in general relatively long, and ranges from several days to several weeks. Furthermore, antibodies are known to be transferred into blood after subcutaneous administration. Specifically, antibody pharmaceuticals meet the requirements described above in (i) and (ii). In addition, since the antibody of the present invention is hardly affected by the presence of anti-A2 inhibitors, it is also considered to satisfy the requirement described above in (iii).

The present invention provides pharmaceutical compositions comprising antibodies of the present invention as an active ingredient. The pharmaceutical compositions comprising antibodies of the present invention are expected to be effective for bleeding, diseases with bleeding, and diseases caused by bleeding, in particular, hemophilia A, acquired hemophilia, and von Willebrand's disease.

Pharmaceutical compositions used for therapeutic or preventive purposes, which comprise antibodies of the present invention as an active ingredient, may be formulated by mixing with suitable pharmaceutically acceptable carriers and media that are non-reactive to the antibodies, as necessary. Such carriers and media include, for example, sterilized water, saline, stabilizers, vehicles, antioxidants (ascorbic acid and such), buffers (phosphate, citrate, other organic acids and such), preservatives, detergents (PEG Tween, and such), chelating agents (EDTA and such), and binding agents. Alternatively, the pharmaceutical compositions may comprise other low-molecular-weight polypeptides, proteins such as serum albumin, gelatin and immunoglobulins, amino acids such as glycine, glutamine, asparagine, arginine, and lysine, carbohydrates and sugars such as polysaccharides and monosaccharides, and sugar alcohols such as mannitol and sorbitol. When prepared as an aqueous solution for injection, it is possible to use saline and isotonic solutions containing glucose and other adjunctive agents such as D-sorbitol, D-mannose, D-mannitol, and sodium chloride. In addition, appropriate solubilizers such as alcohols (ethanol and such), polyalcohols (propylene glycol, PEG, and such), and non-ionic detergents (polysorbate 80, HCO-50, and such) may be used in combination.

Pharmaceutical compositions of the present invention may comprise two or more types of antibodies that enhance the generation of activated blood coagulation factor VIII, as long as they do not inhibit each other's functions. In addition, the antibody of the present invention may be used in combination with blood coagulation factor VIII, if needed. For example, conventional Factor VIII and such used for treating bleeding or the like can be used. Additionally, if needed, it is possible to use other antibodies that suppress the inactivation of activated blood coagulation factor VIII in combination. Antibodies that suppress the inactivation of Factor VIII include, for example, antibodies that suppress the degradation of the factor by inhibiting the binding between the factor and LRP (Patent Document 1) and antibodies that suppress the inactivation of the factor by APC (Non-Patent Document 1).

When blood coagulation factor VIII and/or other antibodies that suppress the inactivation of Factor VIII are used in combination with antibodies of the present invention that enhance the generation of activated blood coagulation factor VIII, the timing for administration is ultimately properly determined by physicians in consideration of the type of dosage form, administration method, patient's age, weight, symptoms, disease type and progression, and other factors. However, the timing is not particularly limited. An antibody that enhances the generation of activated blood coagulation factor VIII may be administered simultaneously, or at a different time point with blood coagulation factor VIII or at least one of the antibodies that suppress the inactivation of Factor VIII. Furthermore, when blood coagulation factor VIII or antibodies that suppress the inactivation of Factor VIII are administered in combination with an antibody of the present invention that enhances the generation of activated blood coagulation factor VIII, the form of administration is not particularly limited, and the components are combined at the time of administration. Such forms of administration include, for example, simultaneously formulating the components into a single preparation and administering the resulting preparation; and separately formulating the components into two or three types of preparations and administering the resulting preparations via a single administration route or different administration routes at the same time or at different time points.

If necessary, antibodies of the present invention may be encapsulated in microcapsules (microcapsules of hydroxymethylcellulose, gelatin, poly[methylmethacrylate], and the like), and made into colloidal drug delivery systems (liposomes, albumin microsphere, microemulsion, nanoparticles, nanocapsules and the like; see "Remington's Pharmaceutical Science 16th edition", Oslo Ed. (1980)). Furthermore, methods for preparing agents as sustained-release agents are also known, and these can be applied in the antibodies of the present invention (Langer et al., J. Biomed. Mater. Res. 15: 267-277 (1981); Langer, Chemtech. 12: 98-105 (1982); U.S. Pat. No. 3,773,919; EP Patent Application No.: 58,481; Sidman et al., Biopolymers 22: 547-556 (1983); EP: 133, 988).

The dose of a pharmaceutical composition of the present invention is ultimately properly determined by physicians, in consideration of the type of dosage form, administration method, patient's age, weight, symptoms, disease type and progression, and other factors. Typically, 0.1 to 2000 mg/day can be administered orally to an adult once or several times. More preferably, the dose ranges from 1 to 1000 mg/day, even more preferably from 50 to 500 mg/day, and still more preferably from 100 to 300 mg/day. The dose varies depending on the patient's weight and age, administration method, and the like; however, the dose can be properly selected by those skilled in the art. The period of administration is preferably properly determined according to the course of treatment and the like for each patient.

In addition, genes encoding antibodies of the present invention may be integrated into gene therapy vectors and used in gene therapy. Administration methods include direct injection of naked plasmids, as well as liposome packaging, formation of various viral vectors such as retrovirus vectors, adenovirus vectors, vaccinia virus vectors, poxvirus vectors, adeno virus related vectors, and HVJ vectors (see Adolph "Virus Genome Methods", CRC Press, Florida (1996)), or by coating onto carrier beads such as colloidal gold particles (for example, WO93/17706). However, any method can be used for administration as long as the antibodies are expressed in vivo and exercise their function. Preferably, a sufficient dose is administered by a suitable parenteral route, such as intravenous, intraperitoneal, subcutaneous, or percutaneous injection, or injection into adipose tissues or mammary glands, inhalation, intramuscular injection, infusion, gas-induced particle bombardment (using electron guns and such), or through the mucosa, for example, by nose drops. Alternatively, genes encoding the antibodies of the present invention may be administered, for example, to blood cells and bone marrow-derived cells ex vivo using liposome transfection, particle bombardment (U.S. Pat. No. 4,945,050), or viral infection, and then the cells can be reintroduced into the animal.

The present invention also provides methods for preventing and/or treating bleeding, diseases with bleeding, and diseases caused by bleeding, which comprise the step of administering compositions or antibodies of the present invention. The antibodies or compositions can be administered, for example, by the methods described above.

Furthermore, the present invention relates to the use of antibodies of the present invention in manufacturing (pharmaceutical) compositions of the present invention.

Furthermore, the present invention also provides kits comprising at least an antibody or composition of the present invention used in the methods described above. The kits may be packaged with syringes, needles, pharmaceutically acceptable media, alcohol-sterilized cotton, bandages, and instructions and other descriptions for use of the kits.

All prior-art documents cited are incorporated herein by reference.

EXAMPLES

1. Materials and Methods
(1) Reagents

A purified preparation of recombinant Factor VIII (Kogenate FS(R)) and Factor VIII/vWF concentrate (Confact F(R)) were kindly provided by Bayer Corp. (Berkeley, Calif.) and KAKETSUKEN (The Chemo-Sero-Theropeutic Research Institute; Kumamoto, Japan), respectively. The light chain and heavy chain of Factor VIII were isolated from EDTA-treated Factor VIII, and then subjected to chromatography using SP- and Q-Sepharose columns (Amersham Bio-Science, Uppsala, Sweden) (Non-Patent Document 8). By HiTrap heparin column and Mono-Q column chromatography, A2 and A1 subunits were isolated from the heavy chain cleaved by thrombin (Nogami et al., (2003) J. Biol. Chem. 278: 1634-41). Factor VIIIa was isolated from thrombin-cleaved Factor VIII, and then subjected to CM-Sepharose chromatography (Amersham Bio-Science) (O'Brien et al., (2000) Blood 95: 1714-20). After the isolated subunits were subjected to SDS-PAGE, the gel was stained using GelCode Blue staining reagent (Pierce, Rockford, Ill.). The purity was found to be >95%. Protein concentrations were determined by Bradford method. vWF was purified from Factor VIII/vWF concentrate using Sepharose CL-4B column (Amersham Bio-Science) gel filtration according to a previous report (Shima et al., (1992) Br. J. Haematol. 81: 533-8). The residual Factor VIII was removed using immunobeads immobilized with monoclonal antibody that recognizes the Factor VIII A3 domain. The purity of purified vWF was found to be >95% by enzyme-linked immunosorbent assay (ELISA) for Factor VIII detection. Human α-thrombin (Sigma, St Louis, Mo.), Factor Xa, recombinant tissue factor (American Diagnostica Inc., Greenwich, Conn.), Factor IXa, Factor X, APC, and protein S (Hematologic Technologies, Burlington, Vt.) were purchased from the respective suppliers. Fluorogenic thrombin-specific substrate Z-Gly-Gly-Arg-AMC (Bachem, Bubendorf, Switzerland) and chromogenic Factor Xa substrate S-2222 (Chromogenix, Milano, Italy) were purchased from the respective suppliers. Phospholipid containing 10% phosphatidylserine, 60% phosphatidylcholine, and 30% phosphatidylethanolamine (Sigma) was prepared using N-octyl glucoside (Mimms et al., (1981) Biochemistry 20: 833-40).

(2) Antibodies

Anti-Factor VIII monoclonal antibody (moAb216) was prepared by a standard hybridoma method. Specifically, mice were immunized with human Factor VIII (Kogenate FS(R)) purchased from Bayer Corp. (Berkeley, Calif.), and spleen cells were isolated from them. The cells were fused with mouse myeloma P3U1 cells. The fused cells were cultured in selection medium containing hypoxanthine, aminopterin, and thymidine. An aliquot of each cell medium supernatant was assayed by ELISA to detect Factor VIII-binding activity. Hybridomas secreting the binder were selected and cloned by limiting dilution. Whether each hybridoma was monoclonal was confirmed by two cycles of limiting dilution. Using G protein-Sepharose column (Amersham Bio-Science), a set of anti-Factor VIII monoclonal antibodies were purified from culture supernatants of the respective hybridoma clones established. Then, the effect of each antibody on coagulation was tested based on the activated partial thromboplastin time (APTT) of standard human plasma. Among the set of antibodies, moAb216 was revealed to shorten APTT. The subclass of moAb216 was determined to be mouse IgG2bκ using Isostrip(R) (Roche Diagnostics, Basel, Switzerland).

Two types of monoclonal antibodies, C5 and 413, were generous gifts from Dr. Carol Fulcher (Scripps Clinic Research Institute, La Jolla, Calif.) and Dr. Evgueni Saenko (University of Maryland School of Medicine, Baltimore, Md.), respectively. C5 (Foster et al., (1988) J. Clin. Investig. 82: 123-8) recognizes the C terminus of the A1 domain and 413 (Fay et al., (2001) J. Biol. Chem. 276: 12434-9) recognizes the A2 domain. NMC-VIII/5, a monoclonal antibody that recognizes the C2 domain, was purified according to a previous report (Non-Patent Document 13). Two types of monoclonal antibodies, JR5 and JR8, which recognize the N termini of the A3 and A2 domains, respectively, were obtained from JR Scientific Inc. (Woodland, Calif.). N-hydroxysuccinimide-biotin (Pierce) was used to biotinylate IgGs (3) Coagulation Assay The levels of Factor VIII activity were determined by one-stage coagulation assay (Casillas et al., (1971) Coagulation 4: 107-11) using Factor VIII-deficient plasma (Sysmex, Kobe, Japan). Factor VIII was activated or inactivated by thrombin, Factor Xa, or APC according to a previous report (Non-Patent Documents 15 and 16). After one hour of preincubation with various concentrations of moAb216 at 37° C., Factor VIII (100 nM) was reacted with thrombin (1 nM), Factor Xa (10 nM), or APC (40 nM), and protein S (50 nM) in a buffer (20 mM HEPES (pH 7.2), 100 mM NaCl, 5 mM $CaCl_2$, 0.01% Tween 20) at 37° C. The reaction with Factor Xa or APC was carried out in the presence of 10 μM phospholipid. Samples were collected from the mixtures at predetermined time points, and the enzyme reaction of each sample was immediately terminated by diluting them 5,000 folds on ice. The coagulation assay showed that none of thrombin, Factor Xa, and APC affected the Factor VIII activity in the diluted samples. Functional stability assay was carried out by incubating Factor VIII (0.4 nM) or normal plasma at 55° C. Samples were collected at predetermined time points to assay the Factor VIII activity in each sample.

(4) Thrombin Generation Assay

Thrombin generation assay was carried out according to a previous report (Hemker et al., (2003) Pathophysiol. Haemost. Thromb. 33: 4-15) except for minor modifications. After preincubation with various concentrations of moAb216, Factor VIII (0.05 nM) was mixed with Factor VIII-deficient plasma (George King Biomedical Inc. Overland Park, Kans.) in the presence of phospholipid (8 μM) and tissue factor (3.3 pM). The reaction was initiated by adding $CaCl_2$ to the sample. Then, the rate of thrombin generation was determined using a fluorogenic thrombin-specific substrate. The reaction product was excited at 390 nm, and the resulting emission spectrum was monitored at 460 nm using Fluoroskan Ascent microplate reader (Thermo Electron Corp., Waltham, Mass.). The percentage of expression of fluorescence intensity was calculated from the respective values measured, and then converted into thrombin concentration (nM) using a standard curve prepared based on the substrate conversion rate determined by adding purified thrombin instead of plasma samples.

(5) Factor Xa Generation Assay

The rate of conversion of Factor X into Factor Xa was monitored using a purified system (Lollar et al., (1993) Methods Enzymol. 222: 128-43). The reaction was carried out at 22° C. After reaction with various concentrations of moAb216, Factor VIII (30 nM) was activated by adding thrombin (10 nM) in the presence of phospholipid (10 μM). After one minute, the thrombin activity was inhibited by adding hirudin. Then, the Factor Xa-generating reaction was initiated by adding Factor IXa (0.5 nM) and Factor X (200 nM). Aliquots were sampled at appropriate time points, and added to tubes containing EDTA (final concentration, 50 mM) to stop the reaction. The initial rate of product formation was determined. The rate of Factor Xa generation was determined by adding chromogenic substrate S-2222 (final concentration, 0.46 mM). The reaction was read at 405 nm using Labsystems Multiskan Multisoft microplate reader (Labsystems, Helsinki, Finland).

(6) Measurement for the Binding Inhibition Effect of moAb216 Using ELISA

Microtiter wells were coated overnight at 4° C. with Factor VIII (8 nM) dissolved in 20 mM Tris, and 150 mM NaCl, pH 7.4 (TBS). After two hours of blocking with 5% HSA at 37° C., a mixture of biotinylated moAb216 (20 μg/ml) and various concentrations of anti-Factor VIII monoclonal antibodies (C5, JR8, 413, JR5, and NMC-VIII/5) were added to the coated wells. The samples were incubated at 37° C. for two hours. The binding of biotinylated moAb216 to Factor VIII was detected using streptavidin-horseradish peroxidase conjugate. Quantitation of the horseradish peroxidase conjugated with streptavidin was carried out after addition of substrate o-phenylenediamine dihydrochloride (Sigma). The reaction was terminated by adding 2M $H_2SO_4$. The absorbance was then measured at 492 nm using a microtiter reader. The amount of biotinylated IgG bound non-specifically in the absence of Factor VIII subunit was less than 5% of the total signal. The amount of specific binding was determined by subtracting the amount of non-specifically bound biotinylated IgG.

(7) Measurement for the Binding of Factor VIII to vWF or Phospholipid by ELISA

The binding of Factor VIII to vWF or phospholipid was measured according to a previous report (Non-Patent Document 13) with minor modifications. Each well of microtiter plates was immobilized at 4° C. overnight with vWF (5 nM) dissolved in TBS buffer or phospholipid (40 nM) dissolved in methanol. After blocking with 5% HSA, 5 nM or 40 nM Factor VIII was preincubated with various concentrations of moAb216. Then, the Factor VIII samples were added to the vWF- or phospholipid-coated wells. The plates were incubated at 37° C. for two hours. The bound Factor VIII was detected by measuring the absorbance at 492 nm using biotinylated JR8.

(8) Electrophoresis and Western Blotting

SDS-PAGE was carried out at 150 V for one hour by the Laemmli method (Laemmli U. K. (1970) Nature 227: 680-5) using 8% gel and a Bio-Rad mini transblot apparatus. For Western blotting, electrophoresed proteins were transferred onto a polyvinylidene difluoride membrane in a buffer (pH 11) containing 10 mM CAPS and 10% (v/v) methanol for two hours at 50 V, using a Bio-Rad mini-gel apparatus. Proteins were detected using a specified monoclonal antibody and then an anti-mouse peroxidase-conjugated secondary antibody. The signal was detected using a highly sensitive chemiluminescence system (PerkinElmer Life Science, Boston, Mass.). The densitometric scan data was quantified by Image J 1.34 (National Institute of Health, USA).

(9) Dot Blotting

Protein (about 200 nM) was dissolved in a buffer (20 mM HEPES (pH 7.2), 100 mM NaCl, 5 mM $CaCl_2$, 0.01% Tween 20), and dropped onto a polyvinylidene difluoride membrane. The protein was detected using the monoclonal antibody (moAb216) and an anti-mouse peroxidase-conjugated secondary antibody. The signal was detected using a highly sensitive chemiluminescence system. The blot was exposed to film.

(10) Data Analysis

All experiments were carried out independently at least in triplicate. The average values obtained are shown herein. Various parameter data were compared and analyzed by paired t test. The significance limit was set as p<0.05. Parameters and standard errors were determined by nonlinear least square regression analysis using KaleidaGraph (Synergy Reading, Pa.). The rate constant (k) for the Factor VIII inactivation by APC and intramolecular stability in the presence of moAb216 were determined by Formula 1 below.

$$[\text{Factor VIII}]_t = [\text{Factor VIII}]_0 \cdot e^{(10^{-C} \times t)} \quad \text{(Formula 1)}$$

wherein $[\text{Factor VIII}]_t$ and $[\text{Factor VIII}]_0$ represent the Factor VIII concentrations at time point (t) and the initial time point, respectively; t, C, and k represent time, -logk, and rate constant, respectively.

To assess the catalytic effect of thrombin or Factor Xa on Factor VIII, the present inventors calculated the activation rate constant based on the Factor VIII activity value obtained. The concentration of free thrombin or Factor Xa is constant under the assumption that the cleavage event and product release are sufficiently rapid. Thus, the rate constant correlates with the substrate concentration as shown in Scheme 1 below.

Scheme 1:

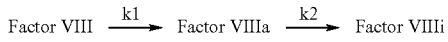

wherein Factor VIIIa and Factor VIIIi represent activated Factor VIII and inactivated Factor VIIIa, respectively. The apparent rate constants ($k_1$ and $k_2$) defined in Scheme 1 were assessed based on a series of reactions for thrombin- or Factor Xa-mediated Factor VIII activation by nonlinear regression according to a previous report (Nogami et al. (2004) J. Biol. Chem. 279: 15763-71) using Formula 2 below.

$$[\text{Factor VIIIa}]_t = [\text{Factor VIII}]_0 \cdot k_1 \cdot (e^{-k_1 t} - e^{-k_2 t})/(k_2 - k_1) \quad \text{(Formula 2)}$$

wherein $[\text{Factor VIIIa}]_t$ represents the concentration of Factor VIIIa at time point (t) and [Factor VIII] represents the initial concentration of Factor VIII.

$$t_{1/2} = 10^C \times \ln(2) \quad \text{(Formula 3)}$$

wherein $t_{1/2}$ represents the half-life in exponential decay, and C is as defined in Formula 1. The half-live ($t_{1/2}$) value was obtained according to Formula 3.

(11) Sequence Analysis of Anti-Factor VIII Monoclonal Antibody (moAb216) Variable Region 1. Determination of the Variable Regions of H Chain and L Chain The genes for H-chain and L-chain variable regions of the anti-Factor VIII monoclonal antibody (moAb216) were amplified by RT-PCR using total RNA extracted from hybridomas producing moAb216. Total RNA was extracted from $1 \times 10^7$ cells of the hybridoma using RNeasy Mini Kits (QIAGEN). A 5' terminal gene fragment was amplified from 1.75 μg of the total RNA using SMART RACE cDNA Amplification Kit (CLONTECH) and synthetic oligonucleotide MHC-IgG2b (SEQ ID NO: 12) complementary to the mouse IgG2b constant region sequence, or synthetic oligonucleotide MHC-kappa (SEQ ID NO: 13) complementary to the nucleotide sequence of mouse κ chain constant region. Reverse transcription was done at 42° C. for 1.5 hour. 50 μl of PCR solutions which contain 10 μl of 5×PCR Buffer, 4 μl of dNTP Mixture (2.5 mM each of dATP, dGTP, dCTP, and dTTP), 1 μl of Prime Star (all of the above are from TaKaRa), 5 μl of 10× Universal Primer A Mix (CLONTECH), 2.5 μl of reverse transcription product, and 10 pmole of synthetic oligonucleotide MHC-IgG2b or kappa were prepared, and reacted at an initial temperature of 98° C. for two minutes, followed by 30 cycles of 98° C. for ten seconds, 60° C. for five seconds, and 72° C. for one minute, and then ten minutes of heating at 72° C. Each of the PCR products was purified from agarose gel using QIAquick Gel Extraction Kit (QIAGEN), and then treated with r-Taq to add A(s) to the end of the amplified fragments. 10 μl of r-Taq reaction solution containing 2 μl of 10× rTaq Buffer, 11 of dNTP Mixture (2.5 mM each of dATP, dGTP, dCTP, and dTTP), 1 μl of r-Taq, and 5 μl of amplified fragment was incubated at 72° C. for 30 minutes. The r-Taq-treated fragment was cloned into pCR2.1-TOPO vector (Invitrogen) and its nucleotide sequence was determined. The nucleotide sequence of each DNA fragment was determined by DNA sequencer ABI PRISM 3730xL Genetic Analyzer (Applied Biosystems) using BigDye Terminator 3.1 Cycle Sequencing Kit (Applied Biosystems) according to the appended instruction manual.

```
                                            SEQ ID NO: 12
(MHC-IgG2b)
CAGGG GCCAG TGGAT AGACT GATG

SEQ ID NO: 13
(MHC-kappa)
GCTCA CTGGA TGGTG GGAAG ATG
```

2. Results (1) Effect of moAb216 on Factor VIII Activity

Figure 1A:
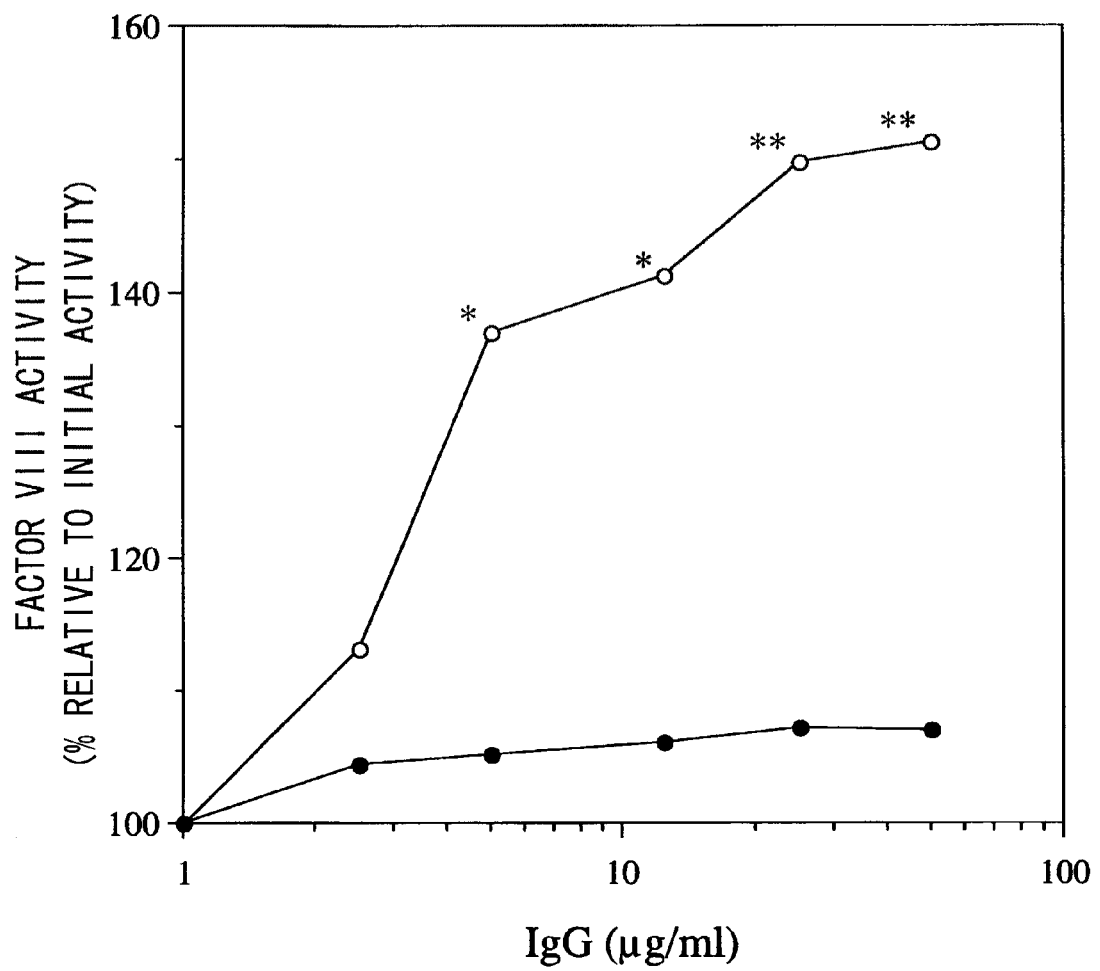
FIG. 1A shows the effect of moAb216 on Factor VIII activity in the one-stage coagulation assay. Various concentrations of moAb216 IgG (open circle) or normal IgG (closed circle) were incubated with Factor VIII (0.4 nM). Then, Factor VIII activity was determined by the one-stage coagulation assay. The Factor VIII activity in the absence of moAb216 was taken as the initial level (100%). Statistical significance between the values for moAb216 and normal IgG calculated by Student's t test is shown (*: $p<0.05$, **: $p<0.01$).

A screening test using APTT for the anti-Factor VIII monoclonal antibody (named moAb216) in plasma showed that the antibody significantly shortened the APTT. moAb216 was tested for the effect of its presence on Factor VIII activity. Factor VIII (0.4 nM) was incubated with various concentrations of moAb216 IgG. Then, the resulting Factor VIII activity was measured by one-stage coagulation assay. The control experiment showed that the presence of IgG and absence of Factor VIII did not affect this assay. When added at a maximal concentration (50 µ/ml; 330 nM at the maximum), moAb216 increased the Factor VIII activity by about 1.5 times as compared to when normal IgG was added. This enhancing effect of moAb216 was dose-dependent (FIG. 1A).

Figure 1B:
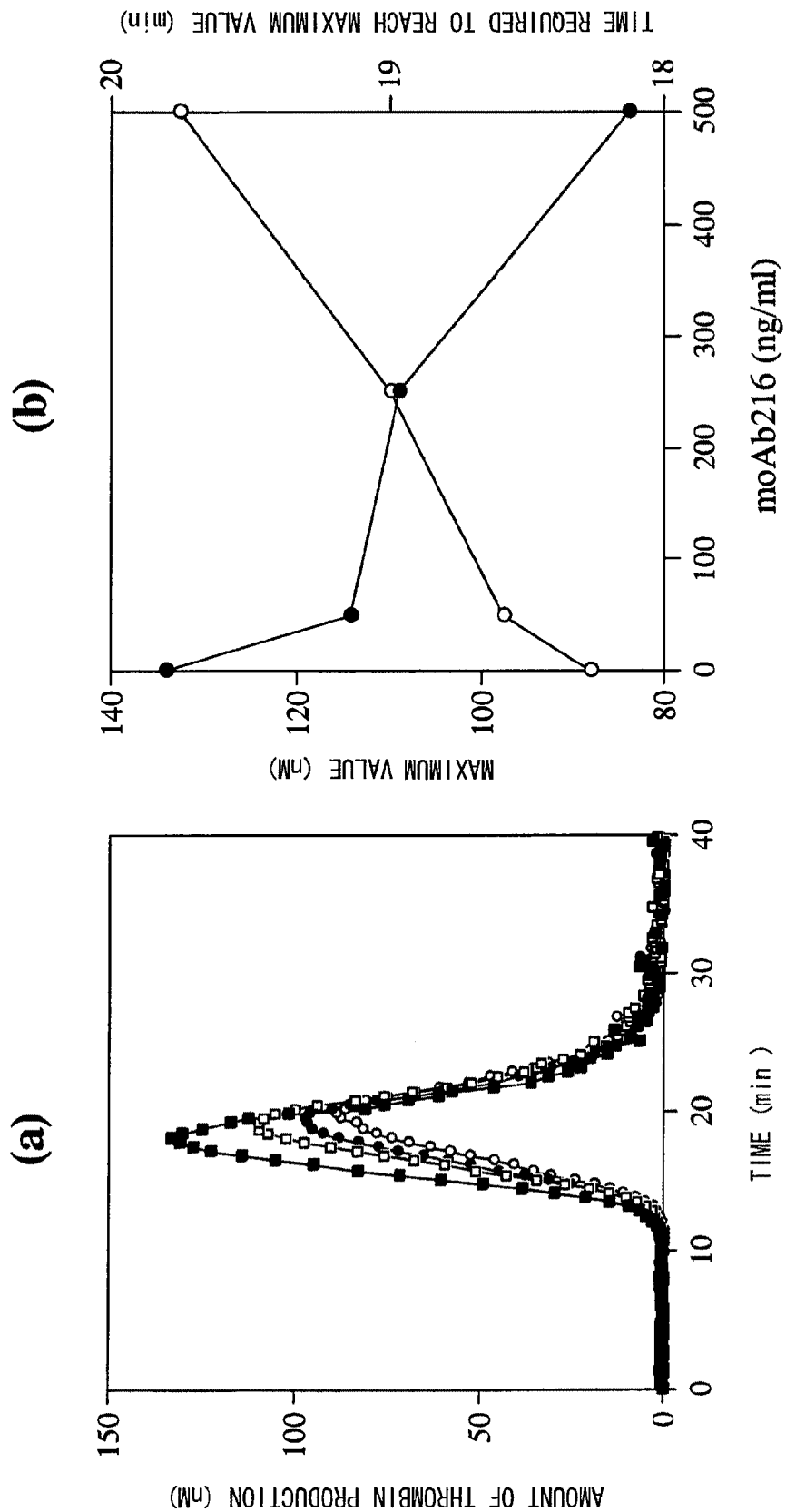
FIG. 1B shows the effect of moAb216 on Factor VIII activity in the thrombin generation assay. (a) Factor VIII (0.05 nM) was preincubated with various concentrations of moAb216, and mixed with Factor VIII-deficient plasma. Then, thrombin generation was assayed. The symbols used are: open circle, 0 ng/ml; closed circle, 50 ng/ml: open square, 250 ng/ml; closed square, 500 ng/ml. Panel (b) shows the parameter determined from the thrombin generation curve (maximal value, open circle; time required to reach the maximal value, closed circle).
Figure 1C:
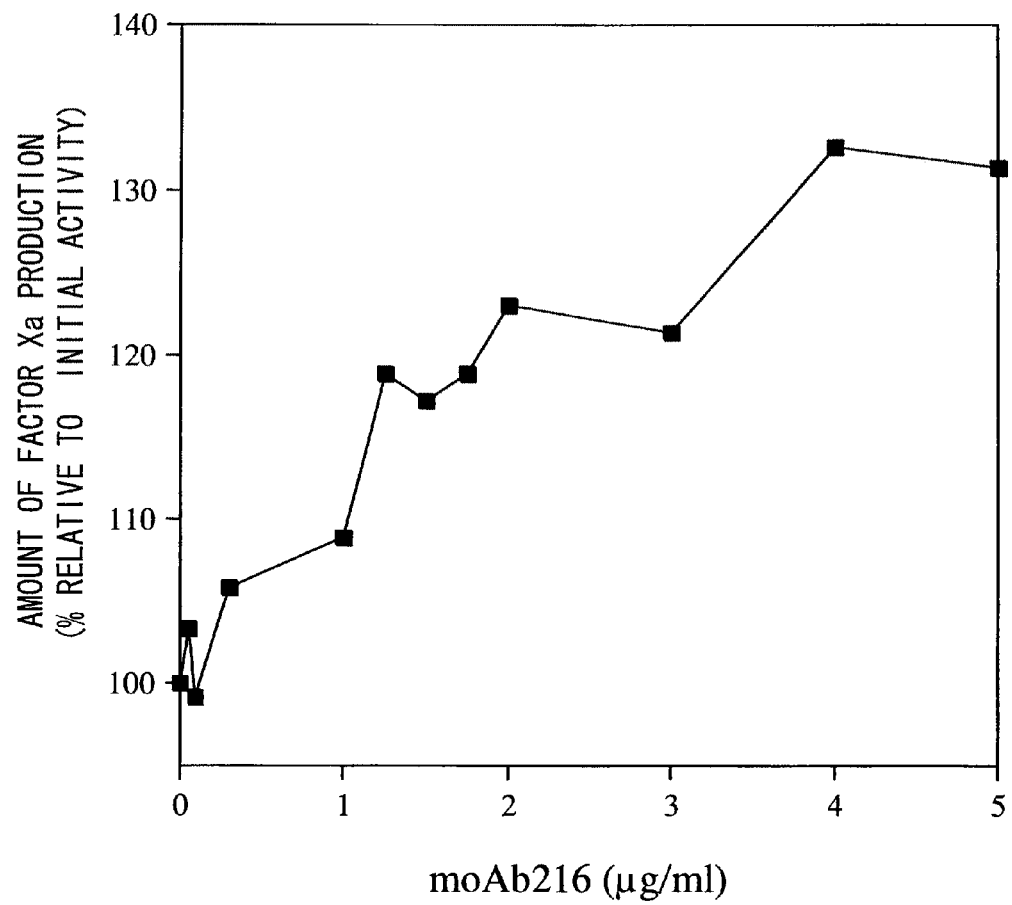
FIG. 1C shows the effect of moAb216 on Factor Xa generation. Factor VIII (30 nM) was reacted with various concentrations of moAb216, and activated by thrombin (10 nM) in the presence of phospholipid. The reaction of Factor Xa generation assay was initiated by adding Factor IXa (0.5 nM) and Factor X (200 nM). The level of Factor Xa generation in the absence of moAb216 was taken as the initial level (100%).
Figure 2:
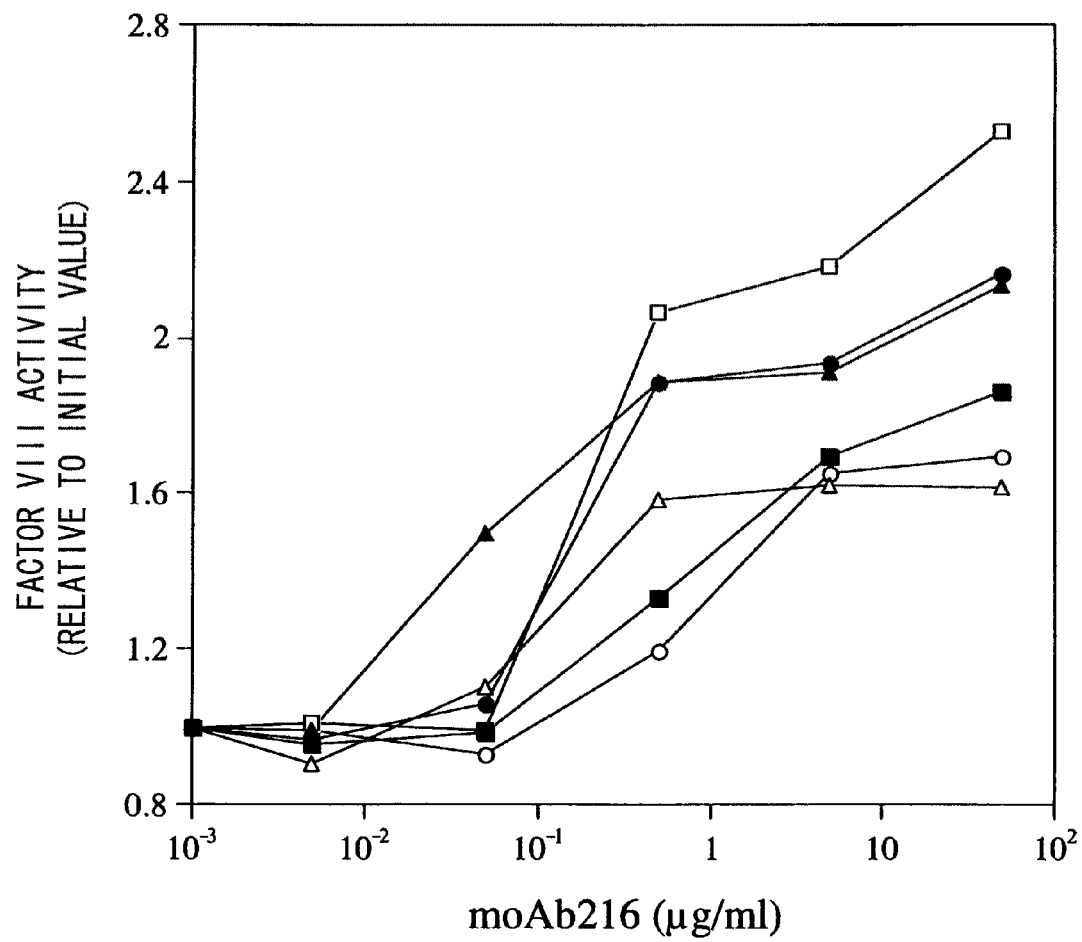
FIG. 2 shows the effect of moAb216 on the inactivation of Factor VIII by the anti-Factor VIII monoclonal antibody in coagulation assay. Various concentrations of the moAb216 IgG were mixed with a constant concentration of an anti-Factor VIII monoclonal IgG antibody [anti-A1 (C5, open circle); anti-A2 (JR8 and 413, which are indicated with closed circle and open square, respectively); anti-A3 (JR5, closed square); anti-C2 (NMC-VIII/5, open triangle)], or normal IgG (closed triangle). The resulting mixtures were reacted with Factor VIII (4 nM) at 37° C. for two hours. Then, the Factor VIII activity of each sample was measured by one-stage coagulation assay. The Factor VIII activity in the absence of moAb216 and presence of each competitor was taken as the initial level.
Figure 3:
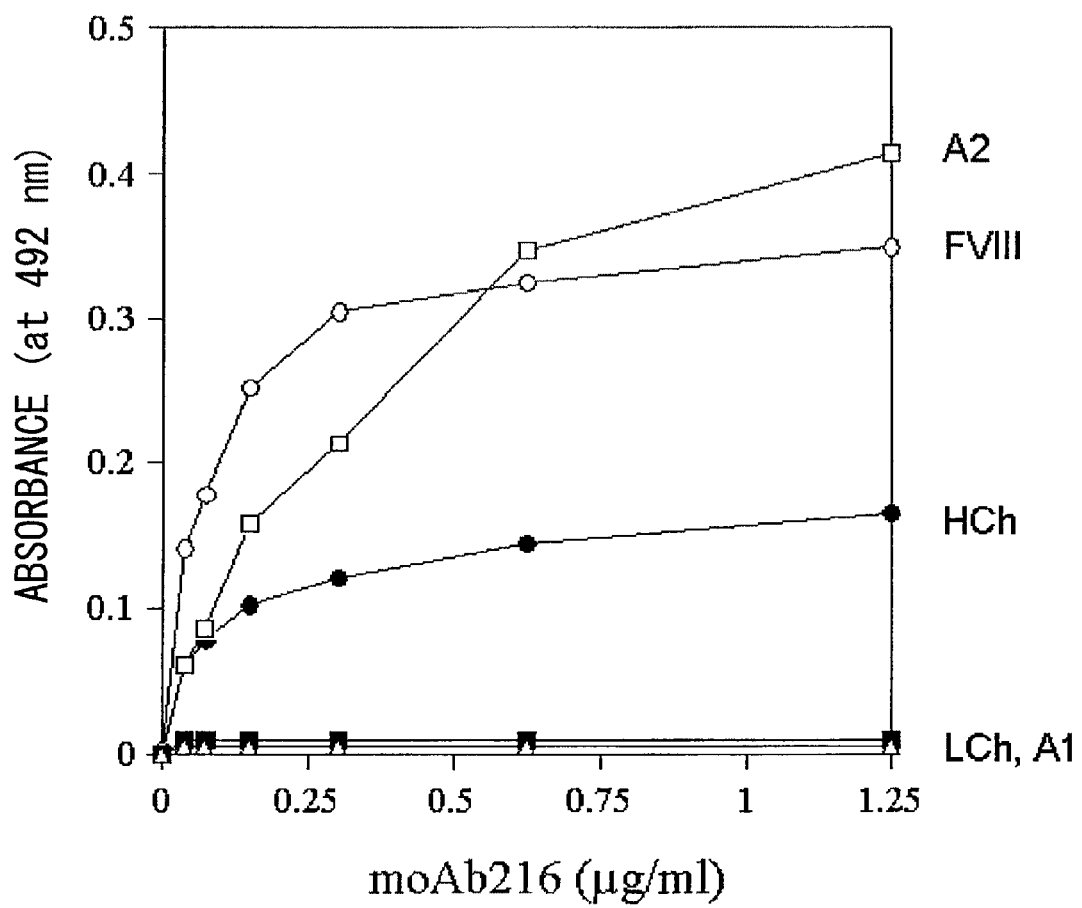
FIG. 3 shows the binding activity of moAb216 to Factor VIII (open circles), heavy chain of Factor VIII (closed circles), light chain of Factor VIII (closed squares), A1 domain of Factor VIII (open triangles) and A2 domain of Factor VIII (open squares) which were immobilized on microtiter wells. Absorbance represents the binding activity of moAb216.

The Factor VIII activity level is well correlated with the levels of thrombin generation and Factor Xa generation. Thus, the present inventors further tested the effect of moAb216 on the generation of thrombin and Factor Xa. In the thrombin generation assay, Factor VIII (0.05 nM) was reacted with various concentrations of moAb216, and then mixed with Factor VIII-deficient plasma. Next, thrombin generation was measured according to the procedure described above in the "Materials and Methods" section (FIG. 1B, a). Two kinetic parameters, namely, the maximal thrombin generation (maximal quantity) and the time required to reach the maximal generation (time required for the maximal quantity), were calculated from the data obtained by thrombin generation assay. moAb216 increased the maximal quantity of thrombin generation and shortened the time required for the maximal quantity in a dose-dependent manner (FIG. 1B, b). Likewise, in the Factor Xa generation assay, when reacted with various concentrations of moAb216, Factor VIII increased Factor Xa generation in a dose-dependent manner. This increasing effect resulted in an increase of up to 1.4 times as compared to the initial value (FIG. 1C). The $K_m$ value of Factor X obtained from the Xase complex in the presence of moAb216 was equivalent to the amount obtained in the absence of moAb216 (40 nM at the maximum; data not shown). When considered together, the results obtained by the present inventors support that moAb216 enhances the cofactor activity of Factor VIII.

(2) Elisa for moAb216 Binding to Factor VIII

Microtiter wells were coated with Factor VIII or its subunit (50 nM) in 20 mM Tris, and 0.15 M NaCl, pH 7.4, overnight at 4° C. The wells were washed with PBS containing 0.01% Tween 20 and were blocked with PBS containing 5% HSA for two hours at 37° C. The indicated concentrations of biotinylated-moAb216 were then added in 20 mM HEPES, 0.1 M NaCl, 5 mM $CaCl_2$, and 0.01% Tween 20, pH 7.2 (HBS-buffer) containing 1% HSA for two hours at 37° C. Bound IgG was quantified by the addition of peroxidase-conjugated streptavidin and O-phenylenediamine dihydrochloride substrate. Reactions were stopped by the addition of 2 M $H_2SO_4$, and absorbance was measured at 492 nm. The amount of nonspecific binding of anti-mouse peroxidase-conjugated IgG in the absence of moAb216 was <5% of the total signal. Specific binding was recorded after subtracting the nonspecific binding.

(3) Kinetic Measurements Using SPR-Based Analysis

The kinetics of moAb216 interaction with Factor VIII was determined by SPR-based assay using a BIAcore X instrument (Biacore AB, Uppsala, Sweden) as previously reported. moAb216 was covalently coupled to the surface of CM5 chip at a coupling density of up to 5 $ng/mm^2$. Binding (association) of the ligand was monitored in the running buffer (10 mM HEPES pH 7.4, 0.1 M NaCl, 1 mM $CaCl_2$, 0.005% polysorbate 20) for two minutes at a flow rate 20 µl/min. The dissociation of bound ligand was recorded over a two-minute period by replacing the ligand-containing buffer with buffer only. The level of nonspecific binding as a result of ligand binding to the uncoated chip was subtracted from the signal. Reactions were performed at 37° C. The rate constants for association ($k_{asso}$) and dissociation ($k_{diss}$) were determined by nonlinear regression analysis using the evaluation software provided by Biacore AB. The dissociation constant ($K_d$) was calculated as $k_{diss}/k_{asso}$.

Binding Parameters for the Interaction of Factor VIII(a) Subunits with moAb216 in SPR-Based Assays

| Factor VIII(a) subunit | $k_{asso}$ $\times 10^4 M^{-1} s^{-1}$ | $k_{diss}$ $\times 10^{-3} s^{-1}$ | $K_d^{\#}$ nM |
|---|---|---|---|
| Factor VIII | 93.0 ± 22.5 | 1.0 ± 0.3 | 1.1 |
| heavy chain | 29.4 ± 6.7 | 0.9 ± 0.2 | 3.0 |
| light chain | n.d.* | n.d.* | — |
| A1 | n.d.* | n.d.* | — |
| A2 | 23.8 ± 2.6 | 0.2 ± 0.07 | 0.8 |
| A3 | n.d.* | n.d.* | — |
| C2 | n.d.* | n.d.* | — |

Reactions were performed as described under "Materials and Methods". Parameter values were calculated by nonlinear regression analysis using the evaluation software provided by Biacore AB.
Values were calculated as $k_{diss}/k_{asso}$.
*not determined To determine the domain recognized by moAb216, the inventors performed an ELISA in which F.VIII(a) subunits were immobilized onto microtiter wells. moAb216 bound to immobilized F.VIII, heavy chain (HCh), and the A2 domain, but not to light chain (LCh) or the A1 domain. Furthermore, in SPR-based assays, F.VIII bound to moAb216 immobilized on a sensor chip ($K_d$; 1.1 nM, $k_{asso}/k_{diss}$; $9.3 \times 10^5$ $M^{-1} s^{-1}/0.0 \times 10^{-3}$ $s^{-1}$). Both HCh and A2 also bound to moAb216 ($K_d$; 3.0 and 0.8 nM, $k_{asso}/k_{diss}$; $2.9 \times 10^5$ $M^{-1} s^{-1}/0.9 \times 10^{-3}$ $s^{-1}$ and $2.4 \times 10^5$ $M^{-1} s^{-1}/0.2 \times 10^{-3}$ $s^{-1}$), while LCh and A1 failed to bind to moAb216, indicating that the antibody recognizes the A2 domain.

Figure 4:
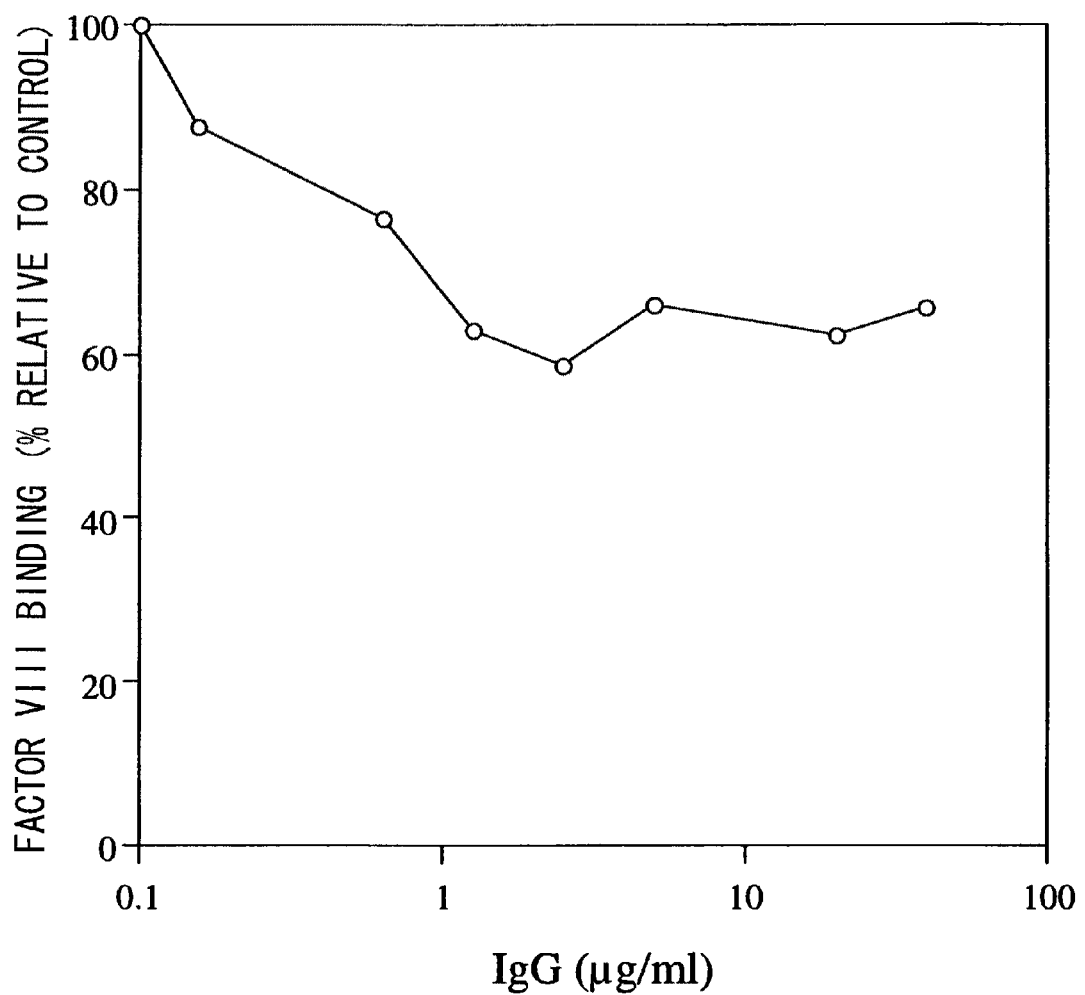
FIG. 4 shows inhibitory effect of moAb216 on the binding of Factor VIII to vWF in ELISA. Mixtures containing various concentrations of moAb216 were added to microtiter wells immobilized with Factor VIII (5 nM). The biotinylated anti-A2 antibody (JR8) bound was detected using streptavidin-horseradish peroxidase conjugate. The absorbance for the binding of Factor VIII to vWF in the absence of moAb216 was taken as 100%.

NMC-VIII/5, an anti-C2 antibody, inhibited the enhancing effect of moAb216 on Factor VIII activity but did not compete with moAb216 for binding to Factor VIII. This disagreement can be caused by the inhibitory property of NMC-VIII/5 in the binding of Factor VIII to phospholipid and/or vWF (Non-Patent Document 13). Most C2 inhibitors blocked the binding of Factor VIII to phospholipid (Non-Patent Document 14) and vWF (Non-Patent Document 12). In this context, to confirm that moAb216 has no C2 epitope, moAb216 was also tested for its inhibitory effect on the binding of Factor VIII to phospholipid and vWF using established ELISA. As expected, moAb216 did not inhibit the binding of Factor VIII to phospholipid (data not shown). This supports that moAb216 has no C2 epitope. On the other hand, the binding of Factor VIII to vWF was partially inhibited by up to 40% (FIG. 4). The major vWF-interaction site in Factor VIII is located in the acidic regions of the A3 domain (Foster et al., (1988) J. Biol. Chem. 263: 5230-4) and C2 domain (Saenko et al., (1994) J. Biol. Chem. 269: 11601-5). Therefore, the degree of inhibition observed was consistent with the data that moAb216 does not recognize the C2 domain. These findings suggest that moAb216 which reacts only with the native (or proper) higher-order structure of Factor VIII recognizes an epitope within the acidic regions of both the A1 and A3 domains.

Figure 5:
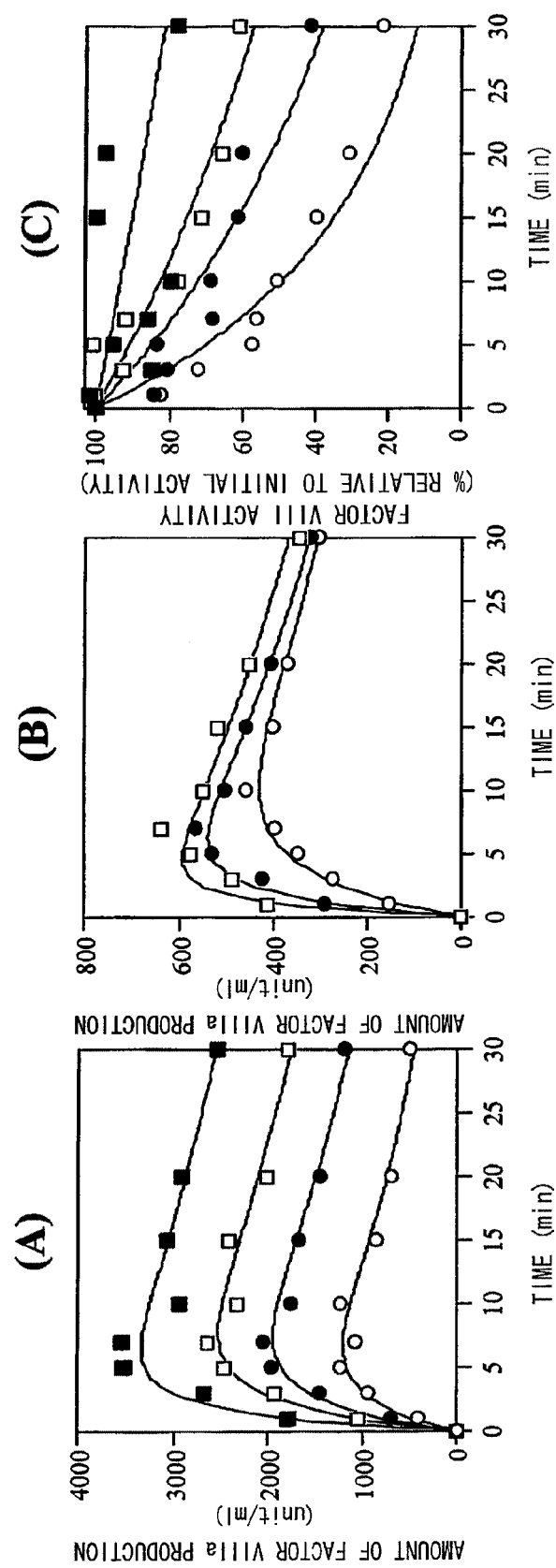
FIG. 5 shows the effect of moAb216 on Factor VIII activation catalyzed by thrombin or Factor Xa, or Factor VIII inactivation catalyzed by APC. After incubation with various concentrations of moAb216, Factor VIII (100 nM) was incubated with thrombin (panel A, 1 nM), phospholipid (10 μM), and Factor Xa (panel B, 10 nM), or phospholipid (10 μM) and APC/protein S (panel C, 40 nM/150 nM). The Factor VIII activity of each sample was measured at the indicated time points by one-stage coagulation assay. The symbols used are as follows. Panels A and C: open circle, 0 μg/ml; closed circle, 2.5 μg/ml; open square, 5 μg/ml; closed square, 10 μg/ml: Panel B: open circle, 0 μg/ml, closed circle, 10 μg/ml; open square, 20 μg/ml. The Factor VIII activity before addition of APC was taken as 100% activity. The data shown in Panels A to C were analyzed using appropriate equations.

(4) Effects of moAb216 on Factor VIII Activation or Inactivation by Serine Protease, Thrombin, Factor Xa, or APC To understand the mechanism underlying the moAb216-mediated enhancement of Factor VIII activity, the present inventors first focused on the effect of the antibody on the Factor VIII activation catalyzed by thrombin or Factor Xa. After preincubated with various concentrations of moAb216, Factor VIII (100 nM) was reacted with thrombin (1 nM) or Factor Xa/phospholipid (10 nM/µM). Then, the activity of Factor VIIIa was measured over time by one-stage coagulation assay (FIGS. 5A and B). The rates of formation and decay of Factor VIIIa were assessed. The result is shown in Table 1.

TABLE 1

| Protease | moAb216(µg/ml) | Rate constant$^b$ (min$^{-1}$) | |
| --- | --- | --- | --- |
| | | $k_1$ | $k_2$ |
| Thrombin | 0 | 0.337 ± 0.073 | 0.047 ± 0.013 |
| | 2.5 | 0.382 ± 0.054 | 0.027 ± 0.001 |
| | 5 | 0.427 ± 0.054 | 0.018 ± 0.002 |
| | 10 | 0.626 ± 0.112 | 0.012 ± 0.002 |
| Factor Xa | 0 | 0.262 ± 0.041 | 0.020 ± 0.003 |
| | 10 | 0.522 ± 0.075 | 0.023 ± 0.003 |
| | 20 | 0.817 ± 0.018 | 0.020 ± 0.004 |

| | | k | |
| --- | --- | --- | --- |
| APC | 0 | 0.0699 ± 0.0070 | |
| | 2.5 | 0.0321 ± 0.0036 | |
| | 5 | 0.0186 ± 0.0017 | |
| | 10 | 0.0066 ± 0.0025 | |

Kinetic parameters for the Factor VIII activation by thrombin or Factor Xa, and Factor VIII inactivation by APC in the presence of moAb216$^a$
$^a$The reaction was conducted.
$^b$Parameter (rate constant) value and standard deviation were calculated from the data shown in FIGS. 5A to C by nonlinear least square regression using the formula indicated in the section of "Materials and Methods".

The maximal activity of thrombin or Factor Xa to activate Factor VIII was observed to be significantly increased in the presence of moAb216 in a dose-dependent manner. The rate constants ($k_1$) for the thrombin- and Factor Xa-mediated activation (10 and 20 µ/ml, respectively) of Factor VIII which reacts with moAb216, were obtained by fitting data to a series of reactions, and they were at most two and three times greater, respectively, than the constant (control) obtained in the absence of the antibody. The enhancing effect was dose-dependent. Also, the value ($k_2$) for the decay of thrombin-activated Factor VIIIa decreased to at most one fourth of that of the control in a dose-dependent manner. Meanwhile, the value for the decay (and/or inactivation) of Factor Xa-activated Factor VIIIa was not clearly affected by the antibody.

The increase in the Factor VIII activity is also affected by the inactivation of Factor VIII. Accordingly, the effect of the antibody on the APC-catalyzed Factor VIII inactivation was further tested. After preincubation with various concentrations of moAb216, Factor VIII (100 nM) was reacted with APC (40 nM), protein S (150 nM), and phospholipid (10 µM), and then the Factor VIII activity was measured (FIG. 5C). The APC-catalyzed Factor VIII inactivation was inhibited by moAb216 in a dose-dependent manner. The rate constant (k) for the moAb216 (10 µg/ml)-mediated inactivation of the Factor VIII substrate was found to be reduced to at most one tenth of that of the control (Table 1). These results indicate that moAb216 enhances the thrombin- and Factor Xa-mediated Factor VIII activation and blocks the APC-mediated Factor VIII inactivation.

(5) moAb216 Affects the Proteolytic Cleavage of Factor VIII by Thrombin, Factor Xa, or APC The up- and down-regulations of Factor VIII activity are mainly related to the proteolytic cleavage at Arg$^{372}$ in the A1-A2 domain junction and at Arg$^{336}$ within the A1 domain, respectively. Thrombin and Factor Xa activate Factor VIII by cleaving at Arg$^{372}$ while APC inactivates Factor VIII by cleaving at Arg$^{336}$. Thus, the present inventors visualized the effect of antibody moAb216 on the cleavage of Factor VIII by thrombin, Factor Xa, or APC by SDS-PAGE analysis. After two hours of preincubation with moAb216 or normal IgG, Factor VIII (100 nM) was reacted with thrombin (1 nM), Factor Xa (10 nM), or APC (40 nM), and protein S (150 nM). FIGS. 6A, 6B and 6C show the result of Western blot analysis for the course of cleavage of the Factor VIII heavy chain using a biotinylated anti-A2 monoclonal antibody (JR8). The band density for the substrate was quantified by densitometric scanning (FIGS. 6A, 6B, and 6C, panel c). The antibody did not significantly affect the cleavage of the A2-B domain junction (Arg$^{740}$) by thrombin (FIG. 6A), but it gently accelerated the cleavage of the A1-A2 domain junction (Arg$^{372}$) as compared to the control cleavage (FIG. 6A, panels a and b). The ratio of A2 product/A1-A2 substrate was investigated by densitometric band scanning. The result showed that the rate of cleavage at Arg$^{372}$ in the presence of the antibody was increased to up to about twice of that of the control (FIG. 6A, panel c). The rate is considered to reflect the rapid conversion of the heavy chain to the activated product, and supports that this result is consistent with the result observed on the thrombin-catalyzed activation of procofactor described above.

Similarly, the cleavage by Factor Xa had no influence on the A2-B domain junction (Arg$^{740}$); however, the cleavage at the A1-A2 domain junction (Arg$^{372}$) was observed to be gently accelerated (FIG. 6B, panel a). The percentage of cleavage (A2/A1-A2 ratio) at Arg$^{372}$ in the presence of the antibody, which was determined by densitometry, was increased up to twice of that of the control within 15 minutes, and this result is consistent with the result observed on the Factor Xa-catalyzed activation (FIG. 6B, panel c). However, in the presence of the antibody, the induced A2 product was gradually decreased after 20 minutes or longer. As a result, the band ratio of A2/A1-A2 was decreased, suggesting that Factor Xa was further proteolyzed within the A2 domain. Meanwhile, in the APC-mediated cleavage in the presence of moAb216, the conversion of the A1-A2 subunits into A1$^{337-372}$-A2 was observed to be relatively reduced when compared to the control (FIG. 6C, panels a and b). When Factor VIII formed a complex with the antibody, the percent cleavage at Arg$^{336}$ in the A1 domain was reduced to at most one-half of that of the control, and this result is consistent with the result observed on the APC-catalyzed inactivation (FIG. 6C, panel c). When considered together, the results obtained suggest that moAb216 enhances Factor VIII activity through the mechanism by which the antibody accelerates the thrombin or Factor Xa-mediated cleavage at Arg$^{372}$ and decelerates the APC-mediated cleavage at Arg$^{336}$.

(6) Effects of moAb216 on Temperature-Dependent Reduction of Factor VIII Activity To investigate whether moAb216 affects the reduction of Factor VIII activity due to thermal denaturation, Factor VIII (0.4 nM) or normal plasma was incubated in the presence of moAb216 at 55° C. for predetermined time periods. Aliquots of each reaction solution were assayed for Factor VIII activity. The result is shown in FIG. 7 and Table 2.

TABLE 2

Intermolecular stability parameters for Factor VIII in plasma and recombinant Factor VIII[a]

|  | Factor VIII[b] | Normal plasma[b] |
| --- | --- | --- |
|  | $t_{1/2}$(min) |  |
| moAb216(−) | 5.8 ± 0.1 | 11.5 ± 0.8 |
| moAb216(+) | 12.9 ± 0.4* | 20.4 ± 2.3** |

[a]Reaction was conducted.
[b]Parameter ($t_{1/2}$) and standard deviation were estimated from the data shown in FIG. 7 by nonlinear least square regression using the formula indicated in the section of "Materials and Methods".
*,**Asterisks indicate that the p value (calculated by t test) in comparison to the data obtained in the absence of moAb216 is less than 0.001 or less than 0.01.

When preincubated with moAb216, normal plasma also exhibited a significant decrease in the activity loss (2× at most) as compared to the loss in the absence of the antibody. Similar effect was also observed when Factor VIII was preincubated with moAb216 This suggests that the presence of the antibody maintains stability for the Factor VIII formation. Thus, the activity of Factor VIII can be maintained and its half-life can be prolonged by the use of the antibody.

(7) Sequence Determination

The variable region of moAb216 was revealed to have the following sequences.

H chain:
(SEQ ID NO: 5)
mnfgfsliflvlvlkgvqcEVRLVESGGGLVKPGGSLKLSCAASEFTFS<u>S</u>
<u>YSMS</u>WVRQTPEKRLEWVA<u>SINSGGRTFYPDSVKG</u>RFTISRDNARNILVLQ
MSSLRSEDTAMYYCAR<u>VIYYDYGAYALDY</u>WGQGTSLTVSS L chain:
(SEQ ID NO: 10)
mdfhvqifsfmlisvtvilssgEIVLTQSPALMAAYPGEKVTITC<u>SVSSS</u>
<u>ISSSNLH</u>WYQQKSETSPKLWI<u>YGTSNLAS</u>GVPVRFSGSGSGTSYSLTISS
MEAEDAATYYC<u>QQWNIYPLT</u>FGAGTKLELK where lower-case-letters represent the signal sequence, and the underlined region corresponds to the CDR.

INDUSTRIAL APPLICABILITY

For the first time, the present invention provides antibodies that enhance the generation of activated blood coagulation factor VIII. The antibodies enhance the cleavage of blood coagulation factor VIII at the Arg of position 372 and suppress the cleavage at the Arg of position 336 by binding to the A2 domain of blood coagulation factor VIII. Such antibodies are expected to be useful in preventing or treating diseases that develop or progress due to decrease or loss of the blood coagulation factor VIII activity, for example, hemophilia A, acquired hemophilia, and von Willebrand's disease.

The invention claimed is:

1. A purified antibody that recognizes the A2 domain of blood coagulation factor VIII and enhances the generation of activated blood coagulation factor VIII, wherein said antibody comprises
   (i) a complementarity determining region wherein the amino acid sequences of the H-chain CDR1, 2, and 3 of said region comprise the amino acid sequences of SEQ ID NOs: 2, 3, and 4, respectively; and
   (ii) a complementarity determining region wherein the amino acid sequences of the L-chain CDR1, 2, and 3 of said region comprise the amino acid sequences of SEQ ID NOs: 7, 8, and 9, respectively.

2. The antibody of claim 1, wherein enhancement of the generation of activated blood coagulation factor VIII is by enhancing the cleavage of blood coagulation factor VIII at the Arg of position 372.

3. The antibody of claim 1, which does not recognize the C2 region of blood coagulation factor VIII.

4. The antibody of claim 1, which suppresses the inactivation of activated blood coagulation factor VIII.

5. The antibody of claim 4, wherein suppression of the inactivation of activated blood coagulation factor VIII is by suppressing the cleavage at the Arg of position 336.

6. A purified antibody that recognizes that A2 domain of blood coagulation factor VIII and enhances the generation of activated blood coagulation factor VIII, wherein said antibody comprises an H-chain variable region whose amino acid sequence is shown in SEQ ID NO: 1.

7. A purified antibody that recognizes the A2 domain of blood coagulation factor VIII and enhances the generation of activated blood coagulation factor VIII, wherein said antibody comprises an L-chain variable region whose amino acid sequence is shown in SEQ ID NO: 6.

8. A purified antibody that binds to the same epitope as the antibody of claim 1.

9. A pharmaceutical composition comprising at least one antibody of any one of claim 1, 6, 7, or 8 as an active ingredient.

10. The pharmaceutical composition of claim 9, which is administered in combination with blood coagulation factor VIII.

11. The pharmaceutical composition of claim 9, which is administered in combination with an antibody that suppresses the inactivation of an activated blood coagulation factor VIII.

* * * * *